United States Patent
Boudreaux

(10) Patent No.: US 10,076,379 B2
(45) Date of Patent: Sep. 18, 2018

(54) ELECTROSURGICAL INSTRUMENT WITH REMOVABLE COMPONENTS FOR CLEANING ACCESS

(71) Applicant: Ethicon Endo-Surgery, Inc., Cincinnati, OH (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 503 days.

(21) Appl. No.: 14/569,961

(22) Filed: Dec. 15, 2014

(65) Prior Publication Data

US 2016/0166315 A1  Jun. 16, 2016

(51) Int. Cl.
*A61B 18/18* (2006.01)
*A61B 18/14* (2006.01)
(Continued)

(52) U.S. Cl.
CPC ............ *A61B 18/1445* (2013.01); *A61L 2/07* (2013.01); *A61B 17/29* (2013.01); *A61B 18/085* (2013.01); *A61B 2018/0063* (2013.01); *A61B 2018/00589* (2013.01); *A61B 2018/00702* (2013.01); *A61B 2018/1455* (2013.01); *A61B 2018/1495* (2013.01); *A61B 2090/0813* (2016.02); *A61B 2218/002* (2013.01); *A61N 2007/025* (2013.01)

(58) Field of Classification Search
CPC ... A61B 17/29; A61B 18/085; A61B 18/1445; A61B 2018/00589; A61B 2018/0063; A61B 2018/00702; A61B 2018/1455; A61B 2018/1495; A61B 2090/0813; A61B 2218/002; A61L 2/07; A61N 2007/025

See application file for complete search history.

(56) References Cited

U.S. PATENT DOCUMENTS

| 4,805,823 A | 2/1989 | Rothfuss |
|---|---|---|
| 5,415,334 A | 5/1995 | Williamson et al. |

(Continued)

FOREIGN PATENT DOCUMENTS

EP    2 074 959 A1    7/2009

OTHER PUBLICATIONS

U.S. Appl. No. 61/410,603, filed Nov. 5, 2010.
(Continued)

*Primary Examiner* — George Manuel
(74) *Attorney, Agent, or Firm* — Frost Brown Todd LLC

(57) ABSTRACT

A surgical instrument includes a handpiece, an elongate shaft assembly extending distally from the handpiece, an activation assembly, an end effector disposed at a distal end of the shaft assembly, and a firing beam. The handpiece comprises a cover operable to selectively expose an interior of the handpiece. The activation assembly is selectively coupleable with the handpiece and is operable to regulate the delivery of power to the end effector. The shaft comprises a selectively removable jaw assembly. The end effector has a pivoting jaw operable to pivot toward and away from the jaw assembly to thereby capture tissue. The jaw assembly and the pivoting jaw each comprise an electrode surface. The electrode surfaces are configured to seal the captured tissue by providing RF energy to the tissue. The firing beam is configured to sever the sealed tissue.

20 Claims, 18 Drawing Sheets

(51) Int. Cl.
*A61L 2/07* (2006.01)
*A61B 18/00* (2006.01)
*A61B 17/29* (2006.01)
*A61B 18/08* (2006.01)
*A61N 7/02* (2006.01)
*A61B 90/00* (2016.01)

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,814,055 A | 9/1998 | Knodel et al. |
| 6,261,294 B1 | 7/2001 | Stihl et al. |
| 6,500,176 B1 | 12/2002 | Truckai et al. |
| 6,783,524 B2 | 8/2004 | Anderson et al. |
| 6,978,921 B2 | 12/2005 | Shelton et al. |
| 7,000,818 B2 | 2/2006 | Shelton et al. |
| 7,112,201 B2 | 9/2006 | Truckai et al. |
| 7,125,409 B2 | 10/2006 | Truckai et al. |
| 7,143,923 B2 | 12/2006 | Shelton et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,303,108 B2 | 12/2007 | Shelton |
| 7,309,849 B2 | 12/2007 | Truckai et al. |
| 7,311,709 B2 | 12/2007 | Truckai et al. |
| 7,343,715 B2 | 3/2008 | Ito et al. |
| 7,354,440 B2 | 4/2008 | Truckai et al. |
| 7,367,485 B2 | 5/2008 | Shelton et al. |
| 7,380,695 B2 | 6/2008 | Doll et al. |
| 7,380,696 B2 | 6/2008 | Shelton et al. |
| 7,381,209 B2 | 6/2008 | Truckai et al. |
| 7,404,508 B2 | 7/2008 | Smith et al. |
| 7,434,715 B2 | 10/2008 | Shelton et al. |
| 7,721,930 B2 | 5/2010 | McKenna et al. |
| 8,408,439 B2 | 4/2013 | Huang et al. |
| 8,453,914 B2 | 6/2013 | Laurent et al. |
| 8,461,744 B2 | 6/2013 | Wiener et al. |
| 8,477,595 B2 | 7/2013 | Schousterman et al. |
| 8,685,056 B2 | 4/2014 | Evans et al. |
| 8,888,809 B2 | 11/2014 | Davison et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,986,302 B2 | 3/2015 | Aldridge et al. |
| 9,028,492 B2 | 5/2015 | Kerr et al. |
| 9,039,695 B2 | 5/2015 | Giordano et al. |
| 9,050,093 B2 | 6/2015 | Aldridge et al. |
| 9,060,776 B2 | 6/2015 | Yates et al. |
| 9,089,327 B2 | 7/2015 | Worrell et al. |
| 9,089,360 B2 | 7/2015 | Messerly et al. |
| 9,161,803 B2 | 10/2015 | Yates et al. |
| 9,220,559 B2 | 12/2015 | Worrell et al. |
| 9,402,682 B2 | 8/2016 | Worrell et al. |
| 9,510,891 B2 | 12/2016 | Allen, IV et al. |
| 2006/0079874 A1 | 4/2006 | Faller et al. |
| 2006/0161185 A1* | 7/2006 | Saadat ............... A61B 17/0469 606/153 |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0088667 A1* | 4/2009 | Masuda ........... A61B 17/32009 601/2 |
| 2012/0078243 A1 | 3/2012 | Worrell et al. |
| 2012/0078244 A1 | 3/2012 | Worrell et al. |
| 2012/0078248 A1* | 3/2012 | Worrell .............. A61B 18/1445 606/45 |
| 2013/0023868 A1 | 1/2013 | Worrell et al. |
| 2013/0046295 A1* | 2/2013 | Kerr ................... A61B 18/1445 606/41 |
| 2016/0143658 A1 | 5/2016 | Stokes et al. |

OTHER PUBLICATIONS

U.S. Appl. No. 61/550,768, filed Oct. 24, 2011.
International Search Report and Written Opinion dated Jun. 20, 2016 for Application No. PCT/US2015/064608, 17 pgs.

* cited by examiner

ELECTROSURGICAL INSTRUMENT WITH REMOVABLE COMPONENTS FOR CLEANING ACCESS

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pat. No. 8,888,809, entitled "Surgical Instrument with Jaw Member," issued Nov. 18, 2014 the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Dec. 20, 2015, the disclosure of which is incorporated by reference herein; U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued Jan. 17, 2017, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
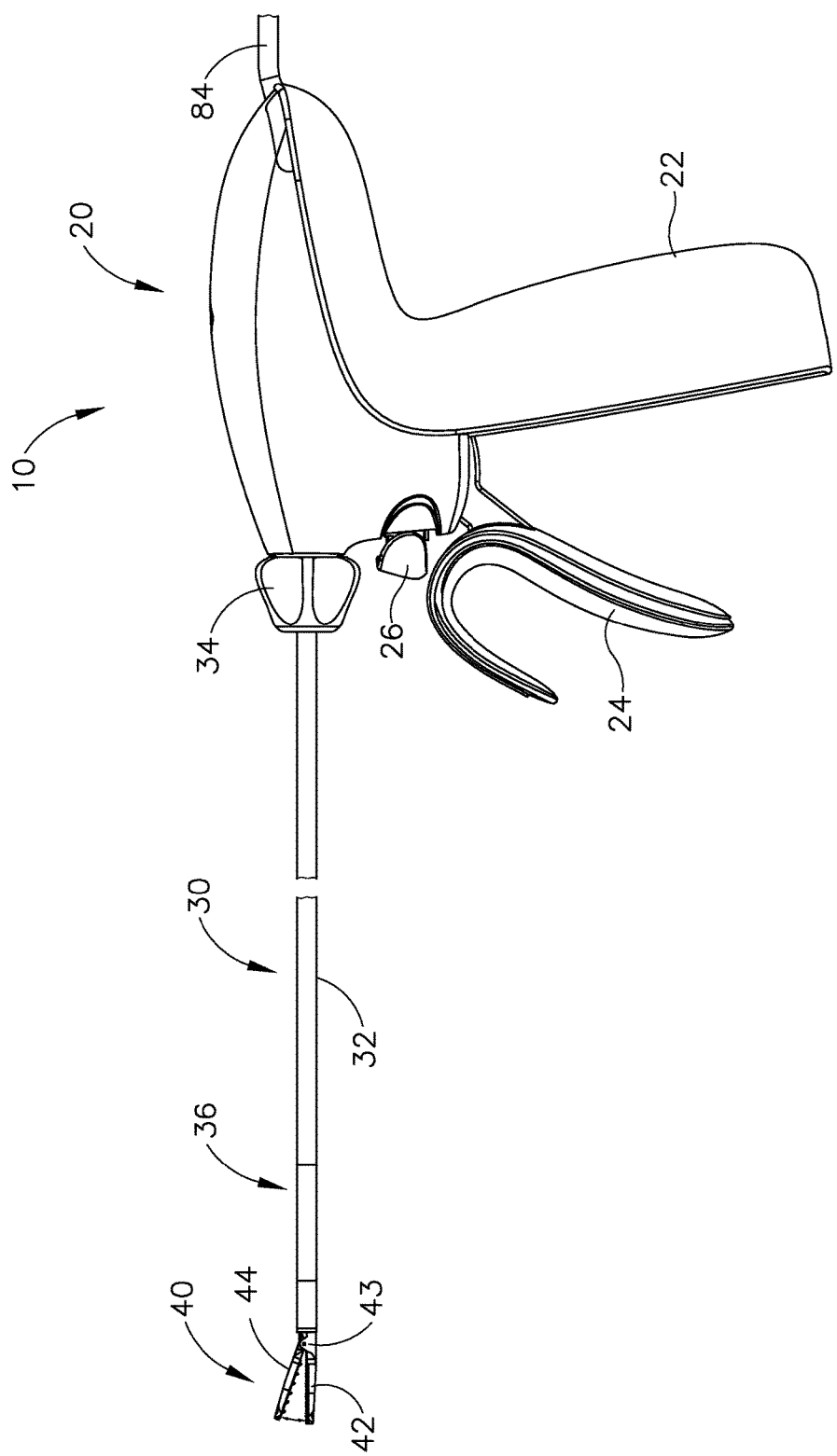
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, now U.S. Pat. No. 8,939,974, issued Jan. 27, 2015; U.S. Pub. No. 2012/0083783, now U.S. Pat. No. 8,888,809, issued Nov. 18, 2014; U.S. Pub. No. 2012/0116379, now U.S. Pat. No. 9,161,803, issued Oct. 20, 2015; U.S. Pub. No. 2012/0078243, now U.S. Pat. No. 9,877,720, issued Jan. 30, 2018; U.S. Pub. No. 2012/0078247, now U.S. Pat. No. 9,402,682, issued Aug. 2, 2016; U.S. Pub. No. 2013/0030428, now U.S. Pat. No. 9,089,327, issued Jul. 28, 2015; and/or U.S. Pub. No. 2013/0023868, now U.S. Pat. No. 9,545,253, issued Jan. 17, 2017. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), and an activation button (26). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Although not shown, it should be understood that in some examples instrument (10) may include an articulation control (not shown). In such examples, the articulation control may be operable to selectively control articulation section (36) of shaft (30), to thereby selectively laterally deflect end effector (40) at various angles relative to the longitudinal axis defined by shaft (30). In some examples the articulation control may be in the form of a rotary dial. In other examples, the articulation control may take numerous other forms. By way of example only, some merely illustrative forms that the articulation control and other components of handpiece (20) may take are disclosed in U.S. Pub. No. 2012/0078243, now U.S. Pat. No. 9,877,720, issued Jan. 30, 2018, the disclosure of which is incorporated by reference herein; in U.S. Pub. No. 2012/0078244, entitled "Control Features for Articulating Surgical Device," published Mar. 29, 2012, now abandoned, the disclosure of which is incorporated by reference herein; and in U.S. Pub. No. 2013/0023868, now U.S. Pat. No. 9,545,253, issued Jan. 17, 2017, the disclosure of which is incorporated by reference herein. Still other suitable forms that the articulation control may take will be apparent to those of ordinary skill in the art in view of the teachings herein. It should also be understood that some versions of instrument (10) may simply lack the articulation control.

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
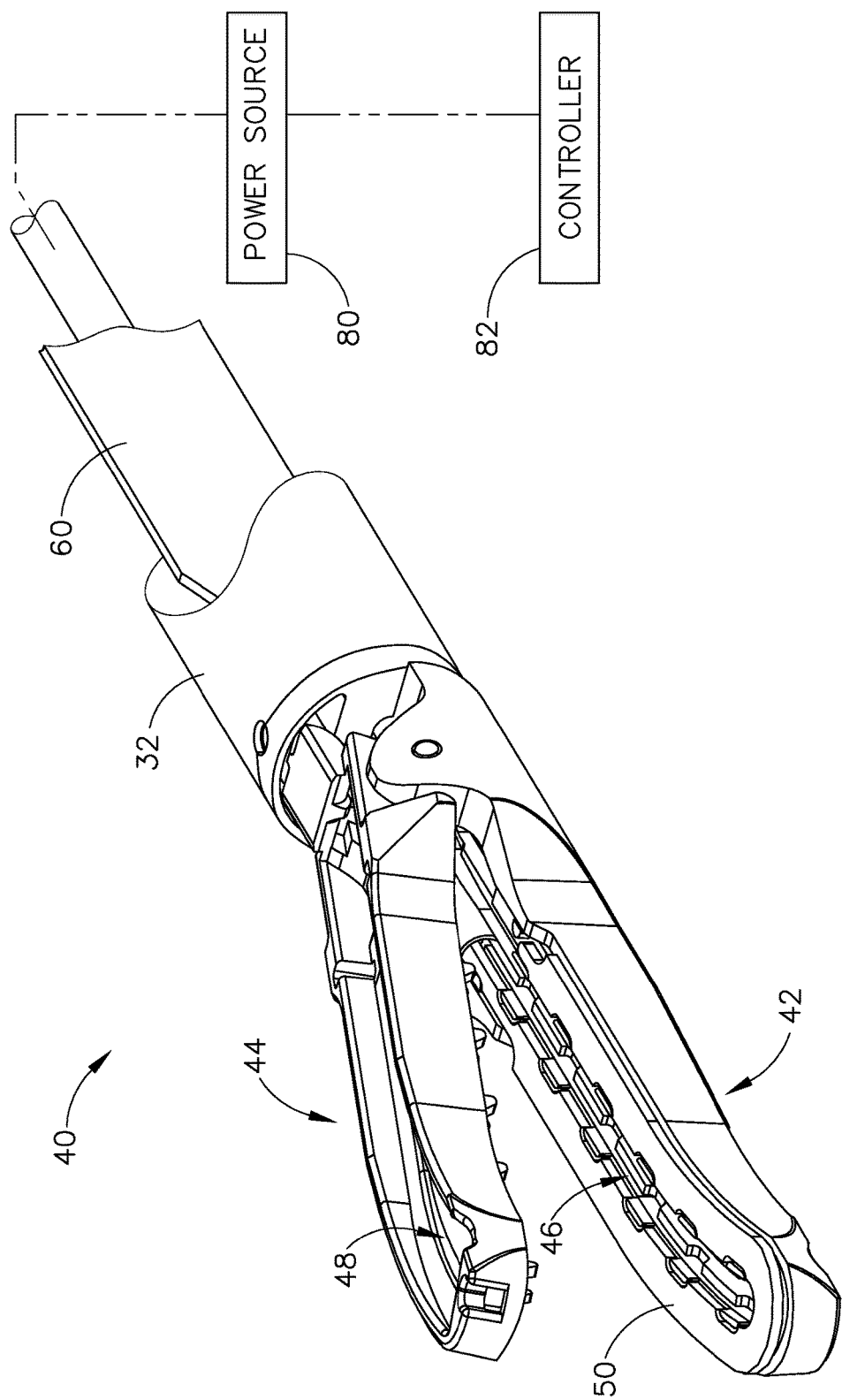
FIG. 2 depicts a perspective view of an end effector of the instrument of FIG. 1, in an open configuration.
Figure 3:
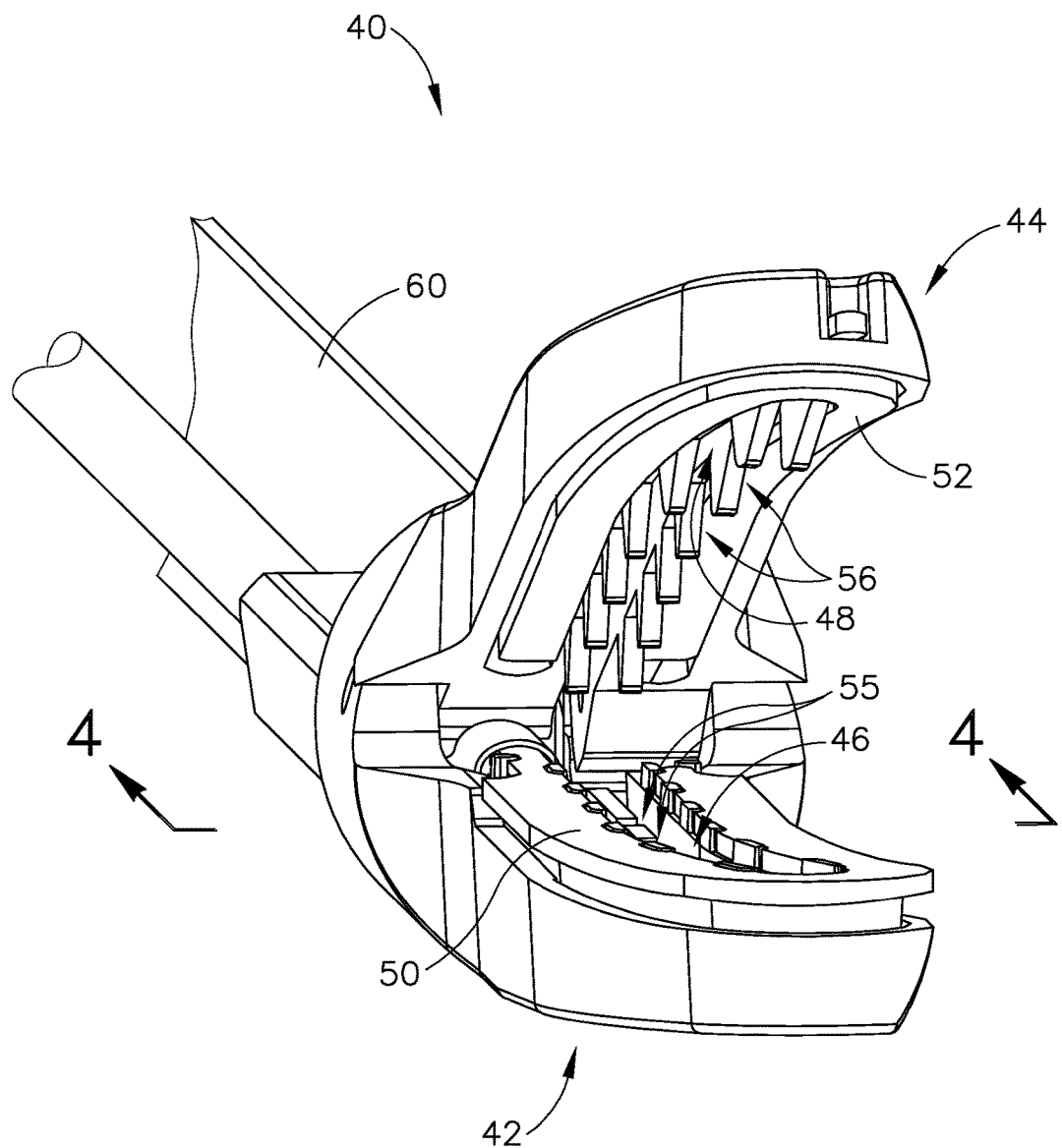
FIG. 3 depicts another perspective view of the end effector of the instrument of FIG. 1, in an open configuration.
Figure 4:
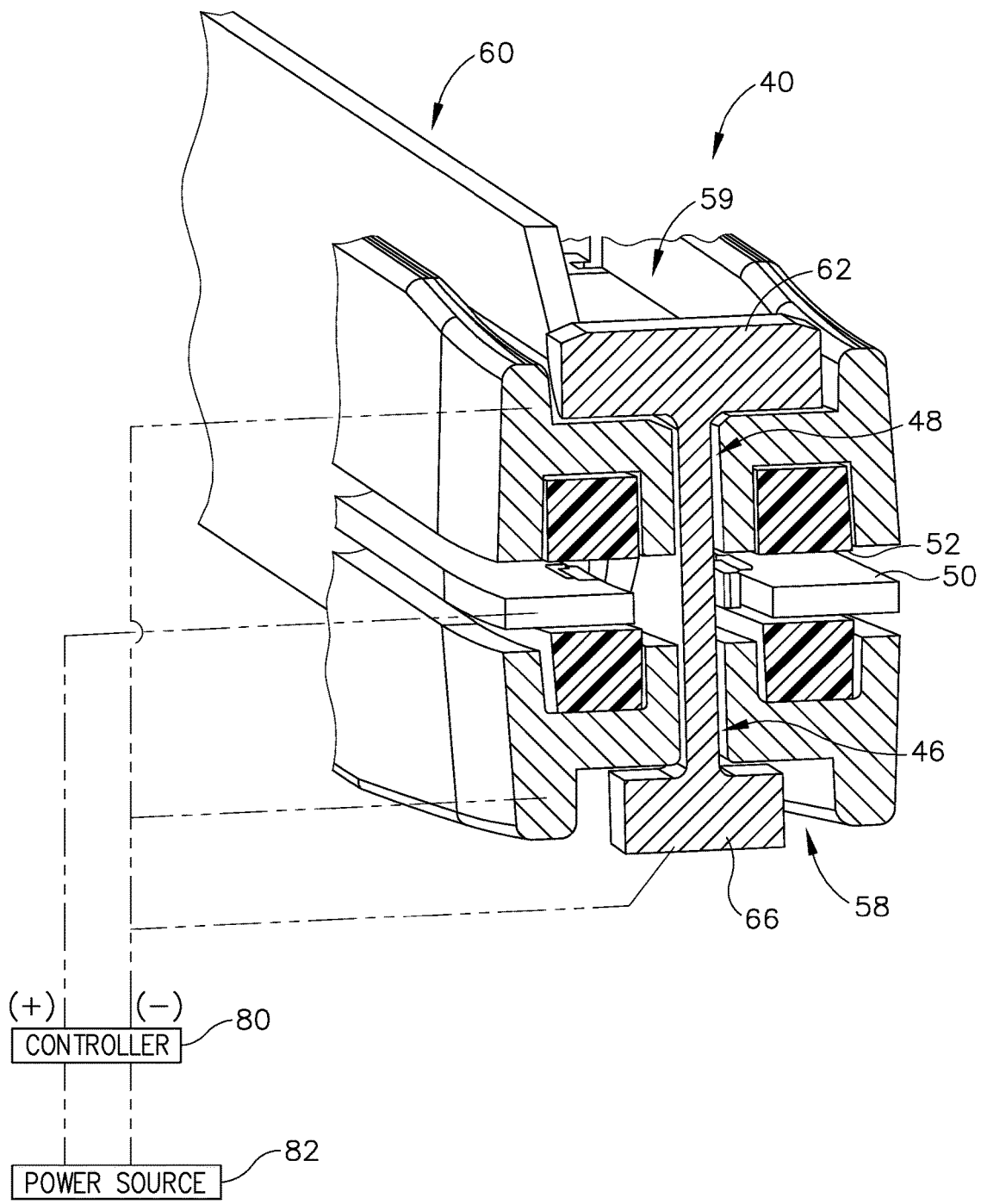
FIG. 4 depicts a cross-sectional end view of the end effector of FIG. 2, taken along line 4-4 of FIG. 3, in a closed configuration and with the firing beam in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode (50); while the underside of second jaw (44) presents a second electrode (52). Electrodes (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode (50) at an active polarity while second electrode (52) serves as a reference/return passive electrode, such that RF current flows between electrodes (50, 52) and thereby through tissue captured between jaws (42, 44). There are instances where the active signal crosses zero potential that the reference is at the same potential so there is no current flow. In some versions, firing beam (60) serves as an electrical conductor that cooperates with electrodes (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrodes (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrodes (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIGS. 2 and 3 show the upper side of first jaw (42) including a plurality of teeth recesses (55). Correspondingly, the lower side of second jaw (44) includes complementary teeth serrations (56) that nest within recesses (55), to enhance gripping of tissue captured between jaws (42, 44) without necessarily tearing the tissue. In other words, it should be understood that serrations (56) may be generally blunt or otherwise atraumatic. Although FIG. 3 shows first jaw having recesses (55) and second jaw (44) serrations (56) as, it should be understood that recesses (55) and serrations (56) may take any other suitable form or may be simply omitted altogether. It should also be understood that serrations (56) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44). In some versions, serrations (56) are electrically conductive.

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrodes (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (not shown) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrodes (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, the PTC thermistor bodies at end effector (40) may automatically reduce the energy delivery at electrodes (50, 52) as the temperature of the tissue and/or end effector (40) increases, thereby reducing the likelihood of overheating. In some such versions, a PTC thermistor element is in series with power source (80) and electrode (50, 52); and the PTC thermistor provides an increased impedance (reducing flow of current) in response to temperatures exceeding a threshold. Furthermore, it should be understood that electrodes (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

Figure 5:
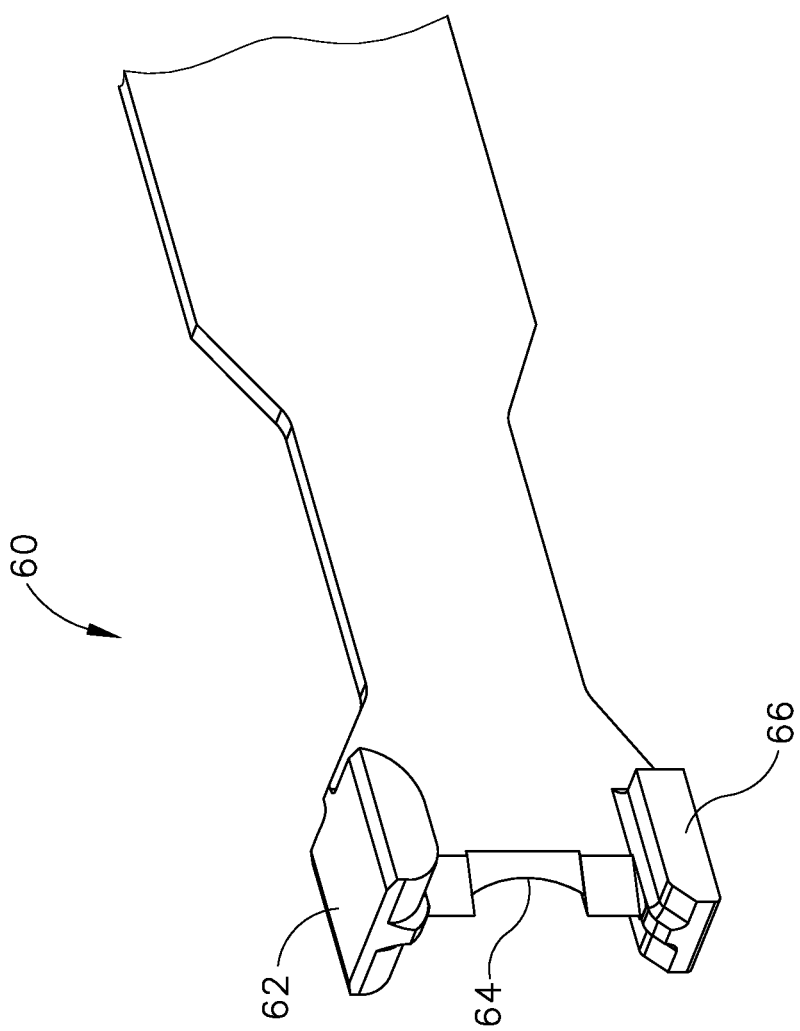
FIG. 5 depicts a partial perspective view of the distal end of the firing beam of the end effector of FIG. 2.

As also seen in FIGS. 2-5, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). As best seen in FIG. 5, firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode.

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

In some variations, firing beam (60) is modified such that flanges (62, 66) are replaced with pins that extend transversely from the modified firing beam. In other words, one or more upper pins could bear against recess (59) of jaw (44), and one or more lower pins could bear against recess (58) of jaw (42), as the modified firing beam is advanced distally through slots (46, 48). In some such versions, one or more of the pins may be configured to rotate about axes that extend transversely from the modified firing beam, such that the pins roll along recesses (58, 59) as the modified firing beam translates longitudinally through slots (46, 48). The pins may thus provide reduced friction with jaws (42, 44), thereby reducing the force required to translate the modified firing beam. In addition or in the alternative, at least one of the pins may be slidably disposed in a corresponding elongate slot formed through the modified firing beam, such that the pin may translate along a plane defined by the modified firing beam. By way of example only, a modified firing beam may be configured in accordance with at least some of the teachings of U.S. Pub. No. 2012/0083783, now U.S. Pat. No. 8,888,809, issued Nov. 18, 2014, the disclosure of which is incorporated by reference herein. Other suitable ways in which firing beam (60) may be varied will be apparent to those of ordinary skill in the art in view of the teachings herein.

D. Exemplary Operation

In an exemplary use, end effector (40) is inserted into a patient via a trocar. Articulation section (36) is substantially straight when end effector (40) and part of shaft (30) are inserted through the trocar. The articulation control, if equipped, may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (42) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, help keep jaws (42, 44) in a closed and tightly clamping position. In particular, flanges (62, 66) help maintain a significantly compressive force between jaws (42, 44). With severed tissue layer portions being compressed between jaws (42, 44), bipolar RF energy is applied to the tissue through electrodes (50, 52) by the user depressing activation button (26). Thus, a bipolar RF current flows through the compressed regions of severed tissue layer portions. The bipolar RF energy delivered by power source (80) ultimately thermally welds the tissue layer portions on one side of firing beam (60) together and the tissue layer portions on the other side of firing beam (60) together.

In certain circumstances, the heat generated by activated electrodes (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrodes (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrodes (50, 52). Other suitable ways in which instrument (10) may be operable and operated will be apparent to those of ordinary skill in the art in view of the teachings herein.

II. Exemplary Electrosurgical Device with Removable Components

In some instances, use of instrument (10) may lead to the buildup of surgical debris (e.g., coagulated blood, tissue particles, etc.) in one or more regions of instrument (10). If instrument (10) is be used in subsequent surgical procedures, this surgical debris may lead to complications if instrument (10) is not properly sterilized. One merely exemplary method of sterilization involves the introduction of saturated steam under pressure to one or more regions of instrument (10). Like some other sterilization methods, however, steam sterilization may cause damage to components of instrument (10). For instance, steam sterilization may cause damage to any electrical components of instrument (10). Thus, it may be desirable to provide instrument (10) with features that allow a user to remove components from instrument (10) that may be damaged by sterilization. For instance, the user may wish to remove components of instrument (10) that are not resistant to fluid and/or heat, including any electrical components of instrument (10). Removal of components may also facilitate cleaning of those removed components (e.g., using techniques different from the techniques used to clean the rest of the instrument). In addition or in the alternative, removal of a component may facilitate cleaning of other instrument features that are revealed or otherwise made more accessible by removal of the removable component. While various examples of features configured to allow a user to remove components from instrument (10) will be described in greater detail below, other examples will be apparent to those of ordinary skill in the art in view of the teachings herein. Similarly, various suitable ways in which the below teachings may be combined with the teachings of the various references cited herein will be apparent to those of ordinary skill in the art.

A. Exemplary Handpiece and Activation Assembly

FIGS. 6-18 show an exemplary electrosurgical instrument (100). Instrument (100) of the present example is configured to operate substantially similar to instrument (10) discussed above except for the differences discussed below. Instrument (100) includes a handpiece (120), a shaft assembly (130) extending distally from handpiece (120), an end effector (140) disposed at a distal end of shaft assembly (130), and an activation assembly (200). Handpiece (120) of the present example includes a pistol grip (122) and a pivoting trigger (124). Trigger (124) is pivotable toward and away from pistol grip (122) to selectively actuate end effector (140) as will be described in greater detail below. Handpiece (120) of the present example further includes a removable cover (128). Cover (12) is operable to selectively cover and uncover an opening (129) formed in a top portion of handpiece (120). As will be discussed in more detail below, covering and uncovering of opening (129) selectively exposes an interior of handpiece (120) such that the interior of handpiece (120) and any components of instrument (100) disposed therein may be more easily accessed for sterilization.

Figure 6:
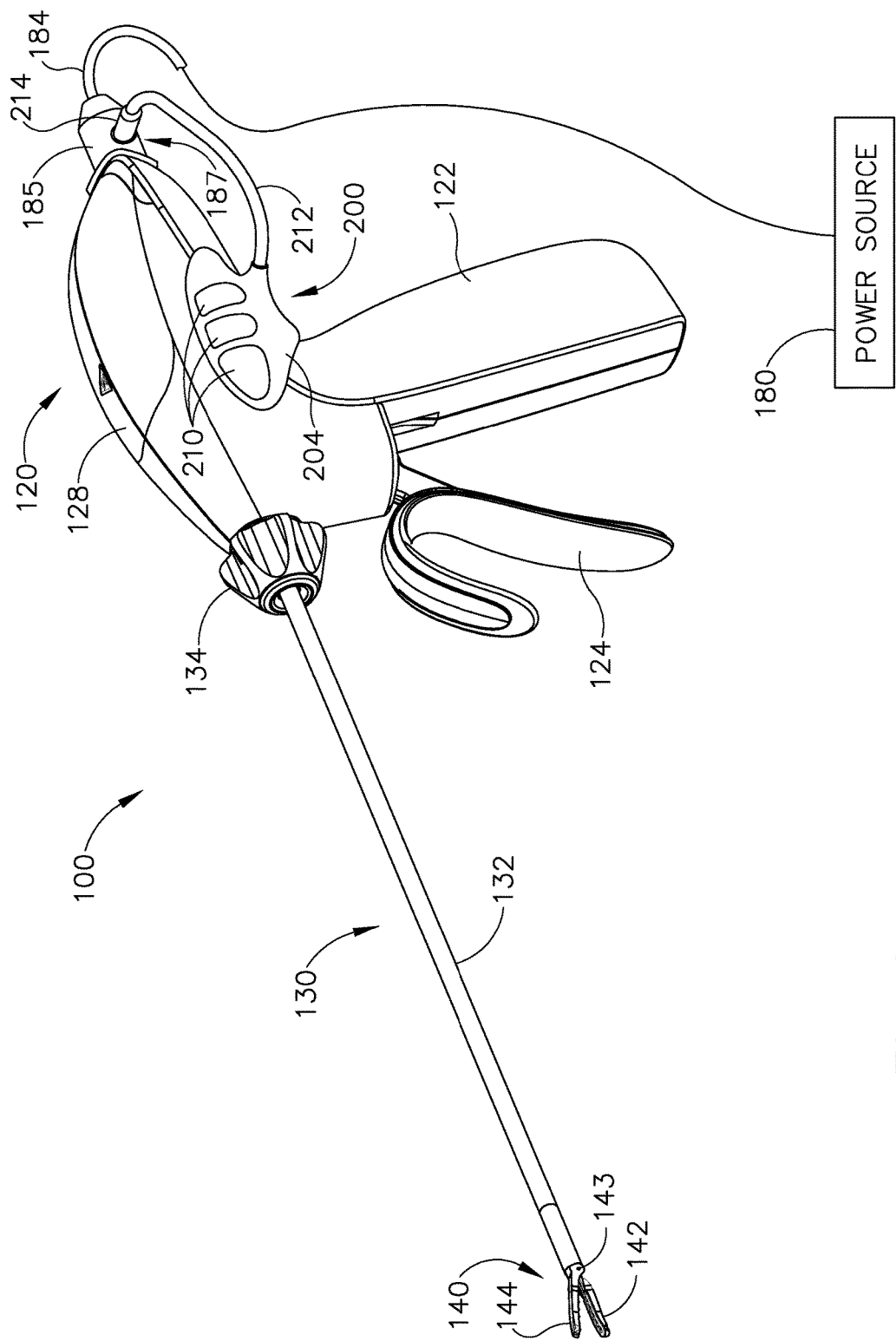
FIG. 6 depicts a perspective view of an exemplary alternative electrosurgical medical instrument.
Figure 7:
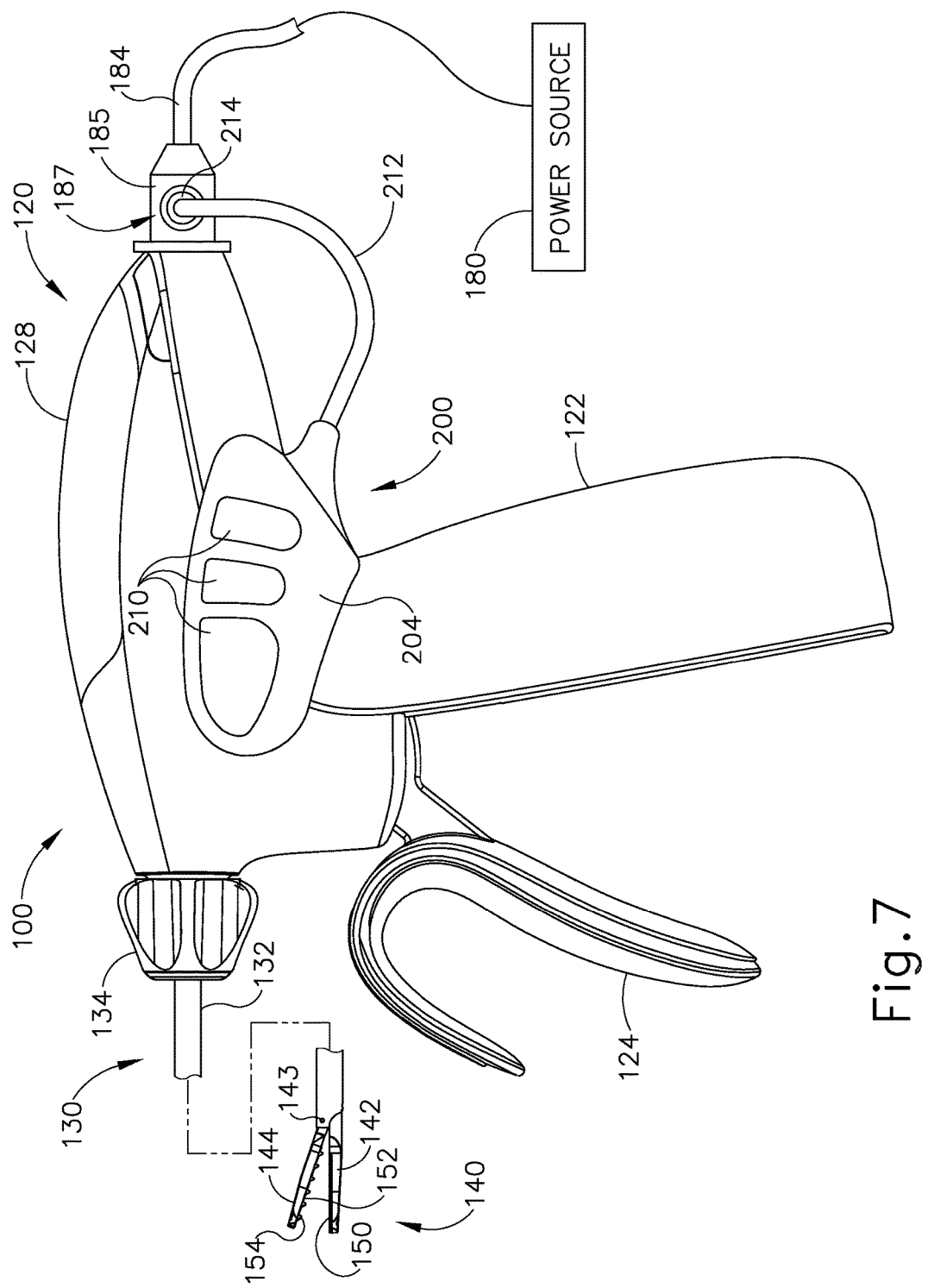
FIG. 7 depicts a side elevational view of the instrument of FIG. 6.
Figure 8:
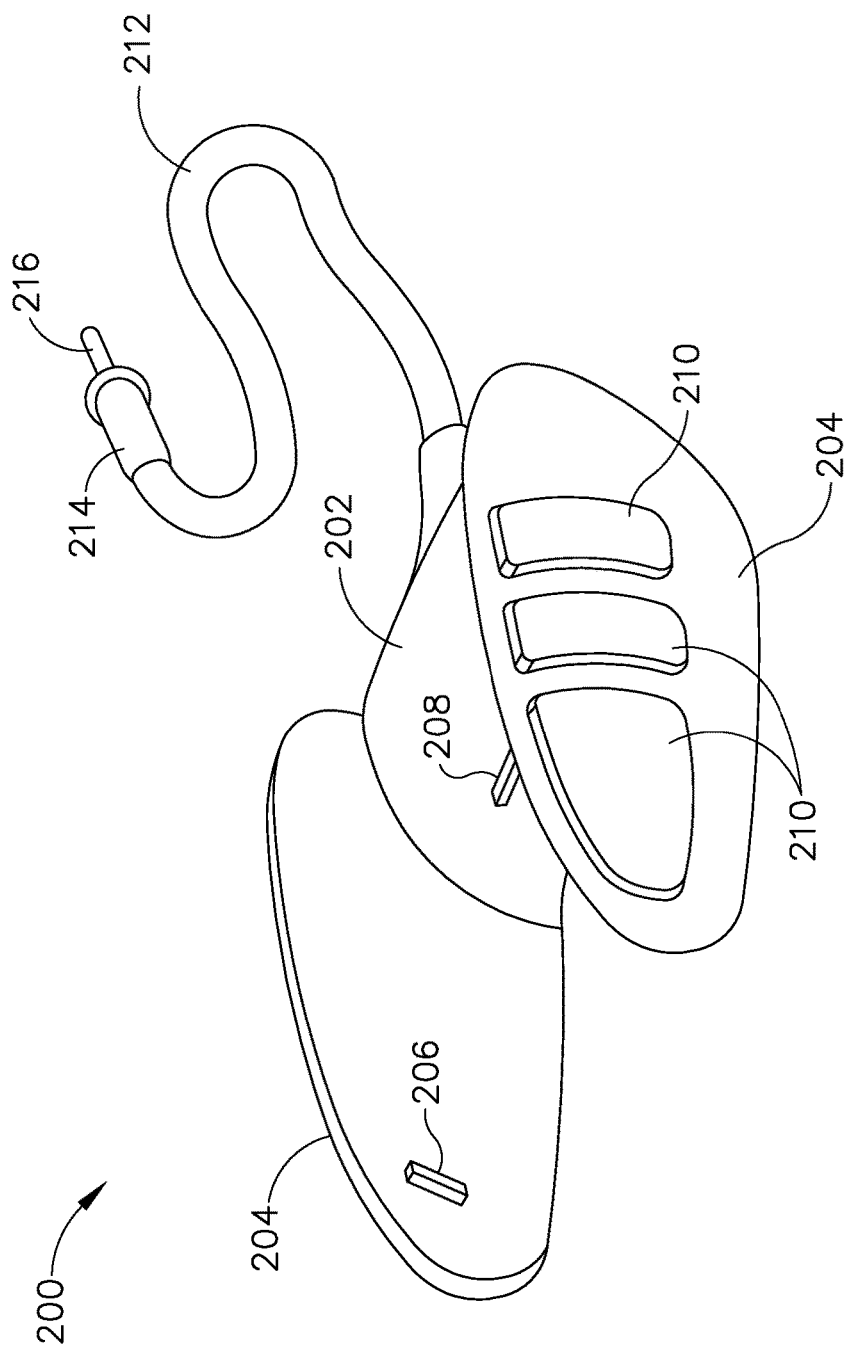
FIG. 8 depicts a perspective view of an activation assembly of the instrument of FIG. 6.
Figure 9:
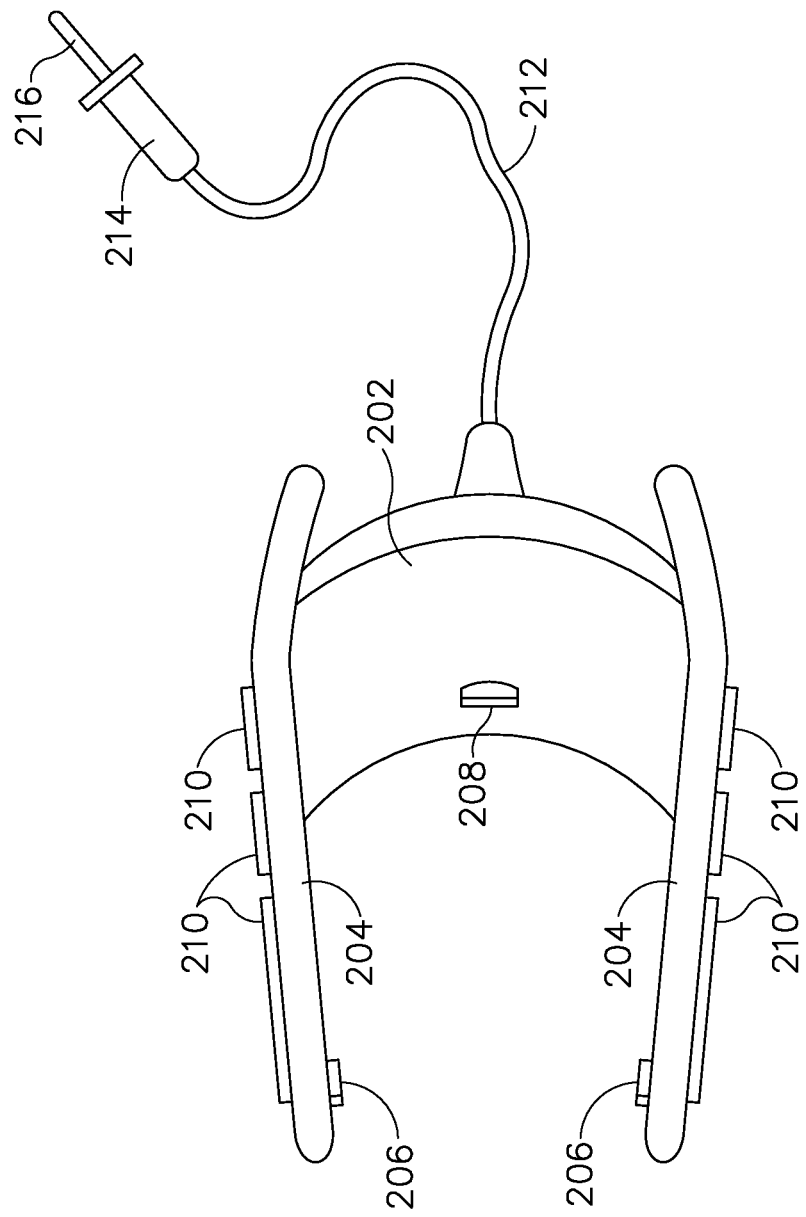
FIG. 9 depicts a top view of the activation assembly of FIG. 8.

As best seen in FIGS. 8 and 9, activation assembly (200) comprises a base (202) and a pair of resilient flanges (204) extending from opposite sides of base (202). Flanges (204) are biased angularly inwardly toward one another into the position best seen in FIG. 9. Flanges (204) are, however, sufficiently flexible such that flanges (204) may flex laterally toward and away from one another. As shown in FIGS. 6 and 7, activation assembly (200) is selectively coupleable with handpiece (120). In particular, each flange (204) includes a tab (206) extending inwardly from an interior surface of each flange (204). As activation assembly (200) is passed onto handpiece (120), contact between tabs (206) and an exterior surface of handpiece (120) causes flanges (204) to flex laterally outwardly relative to one another. Tabs (206) are configured to be received within a pair of recesses (123) formed in the exterior surface of handpiece (120) such that flanges (204) may return toward the position best seen in FIG. 9 and such that activation assembly (200) is coupled with handpiece (120) in a snap-fit manner. It should be understood, however, that activation assembly (200) may be coupled with handpiece (120) in any other appropriate manner as would be apparent to those of ordinary skill in the art in view of the teachings herein. Base (202) further includes a tab (208) extending from an interior surface of base (202). With activation assembly (200) coupled to handpiece (120), tab (208) is configured to be received within a recess (125) formed in a proximal surface of pistol grip (122) so as to limit movement of activation assembly (200).

As will be discussed in more detail below, the electrical components of instrument (100) are housed within activation assembly (200) such that the electrical components of instrument (100) may be removed from instrument (100) prior to sterilization of instrument (100). With the electrical components of instrument (100) housed within activation assembly (200), handpiece (120) is void of any electrical components that may be damaged during steam sterilization or other forms of sterilization that might otherwise damage electrical components. Activation assembly (200) further comprises a cable (212) that is operable to electrically couple activation assembly (200) with instrument (100) and a power source (180) such that activation assembly (200) is in electrical communication with instrument (100) and power source (180). As will be discussed in more detail below, activation assembly (200) is operable to control the functions of instrument (100). For instance, activation assembly (200) is operable to regulate delivery of power to end effector (140).

B. Exemplary Shaft Assembly

Figure 10:
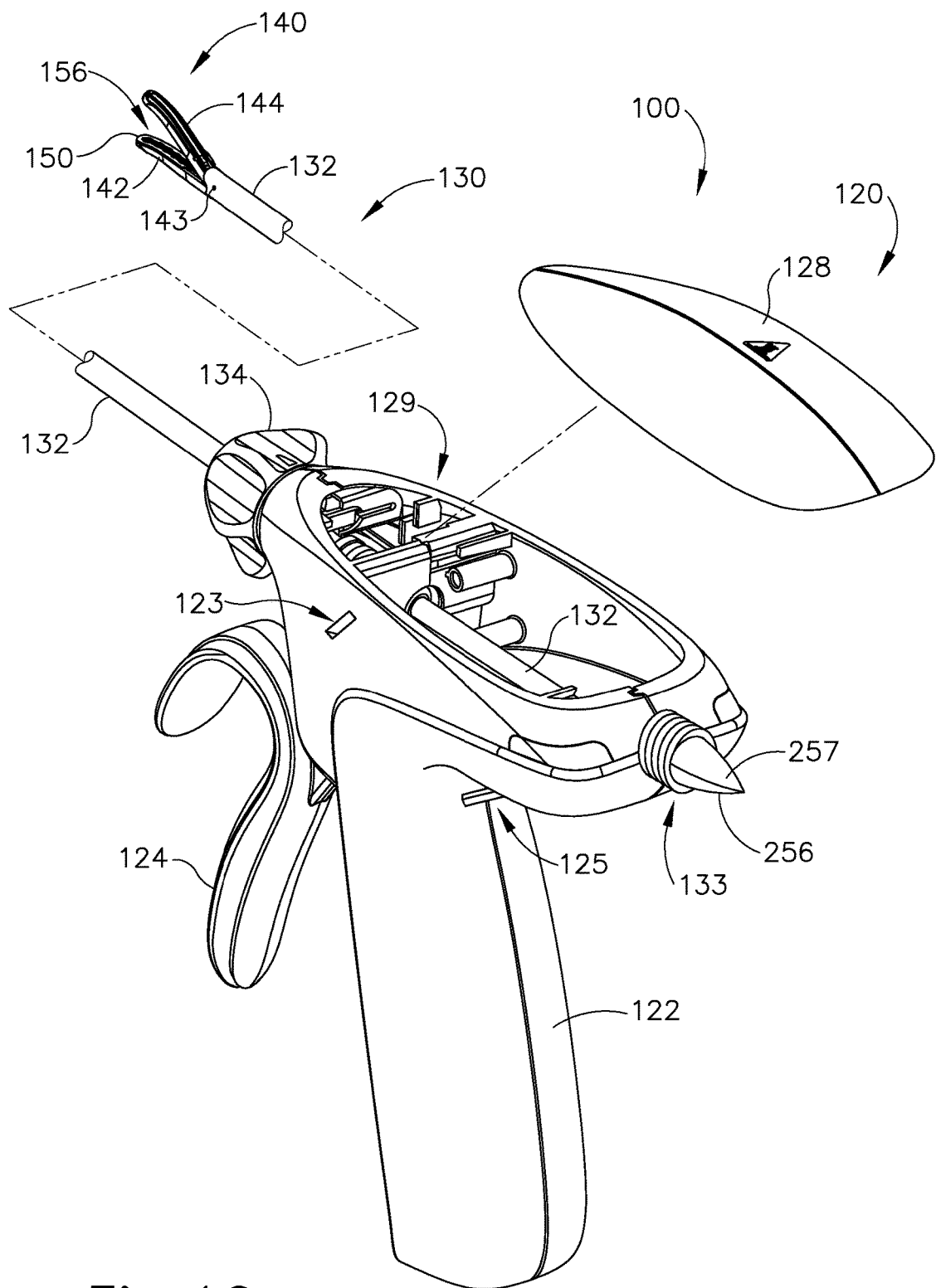
FIG. 10 depicts a perspective view of the instrument of FIG. 6 with the activation assembly of FIG. 8, a generator cable, and a snap-on handpiece cover removed.
Figure 11:
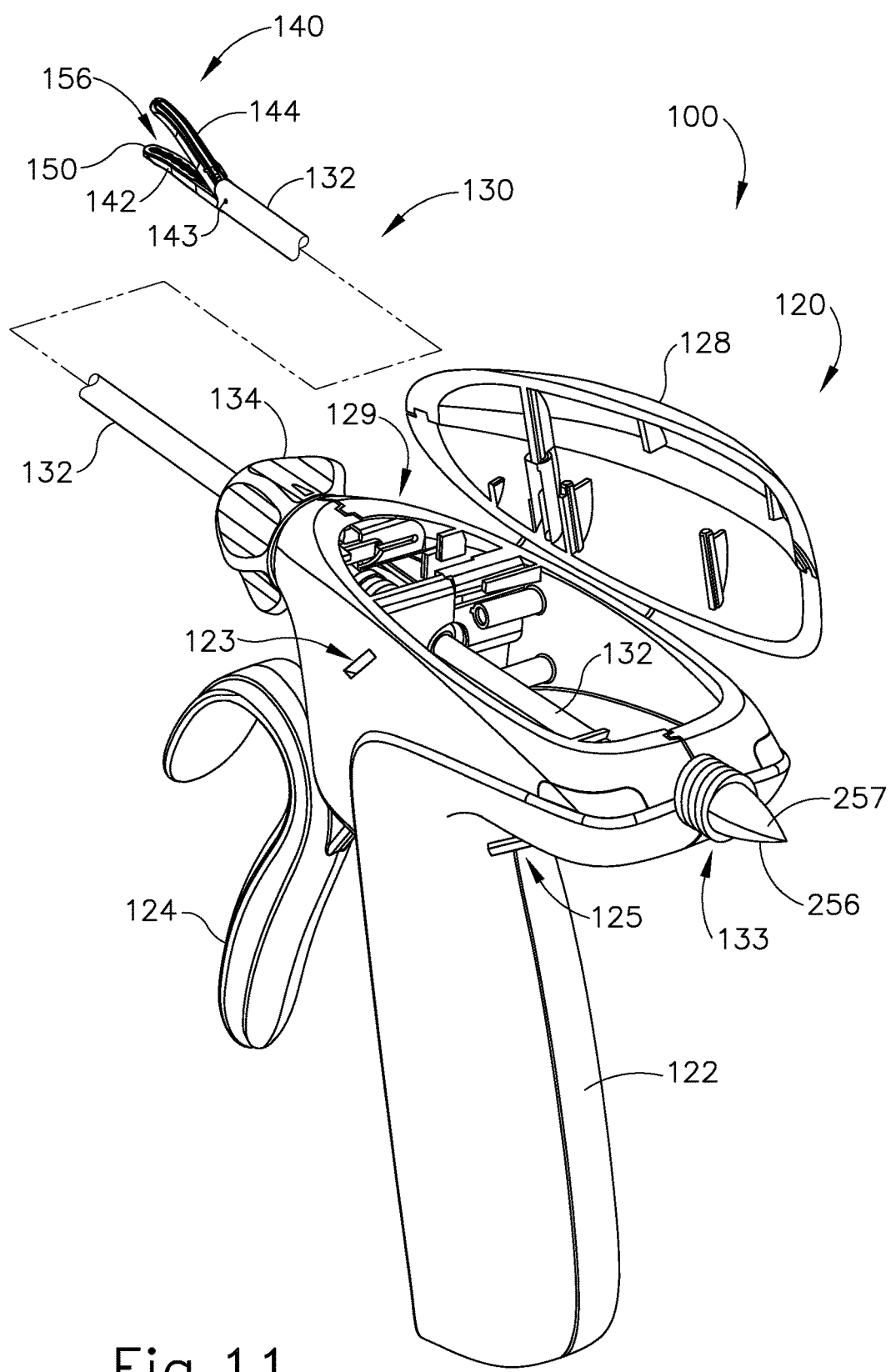
FIG. 11 depicts a perspective view of the instrument of FIG. 6 with the activation assembly of FIG. 8 and the generator cable of FIG. 10 removed, and with an exemplary hinged handpiece cover opened.

Shaft assembly (130) of the present example comprises a rigid outer sheath (132) and an inner tube (136). Sheath (132) passes completely through handpiece (120), from the proximal end of handpiece (120) to the distal end of handpiece (120), and extends proximally and distally therefrom. As best seen in FIGS. 10 and 11, proximal end of sheath (132) comprises threading (133). As will be discussed in more detail below, threading (133) is operable to couple shaft assembly (130) with, among other things, a cable (184) and a flushing hose (260). Inner tube (136) is slidably disposed within a hollow interior of sheath (132). As will be discussed in more detail below, inner tube (136) is operable to translate longitudinally within sheath (132), relative to sheath (132), to selectively translate a firing beam (160) longitudinally relative to shaft assembly (130).

In some versions, shaft assembly (130) is also rotatable about the longitudinal axis defined by sheath (132), relative to handpiece (120), via a knob (134). Such rotation may provide rotation of end effector (140) and shaft assembly (130) unitarily. In some other versions, knob (134) is operable to rotate end effector (140) without rotating any portion of shaft assembly (130) that is proximal of end effector (140). As another merely illustrative example, electrosurgical instrument (100) may include one rotation control that provides rotatability of shaft assembly (130) and end effector (140) as a single unit; and another rotation control that provides rotatability of end effector (140) without rotating any portion of shaft assembly (130) that is proximal of end effector (140). In some versions of instrument (100), cable (184) may rotate with end effector (140) and/or shaft assembly (130). Alternatively, a plug (185) of cable (184) may include sliding or rotating electrical contacts that enable plug (185) and cable (184) to remain stationary while permitting a pair of electrical contacts (256, 257) of shaft assembly (130) to rotate within plug (185), while still providing electrical continuity between electrical contacts (256, 257) and complementary wires within cable (184) as will be discussed in more detail below. Other suitable rotation schemes will be apparent to those of ordinary skill in the art in view of the teachings herein. Of course, rotatable features may simply be omitted if desired.

Shaft assembly (130) of the present example, further comprises a lower jaw assembly (250). Lower jaw assembly (250) is slidably disposable within the hollow interior of sheath (132) of shaft assembly (130) such that lower jaw assembly (250) may be slidably disposed within shaft assembly (130) and slidably removed therefrom. As will be described in more detail below, lower jaw assembly (250) can be removed from shaft assembly (130) such that lower jaw assembly (250) and the hollow interior of shaft assembly (130) may be sterilized separately (e.g., using different sterilization techniques); and/or such that a used lower jaw assembly (250) may be replaced with a new lower jaw assembly (250).

Figure 12:
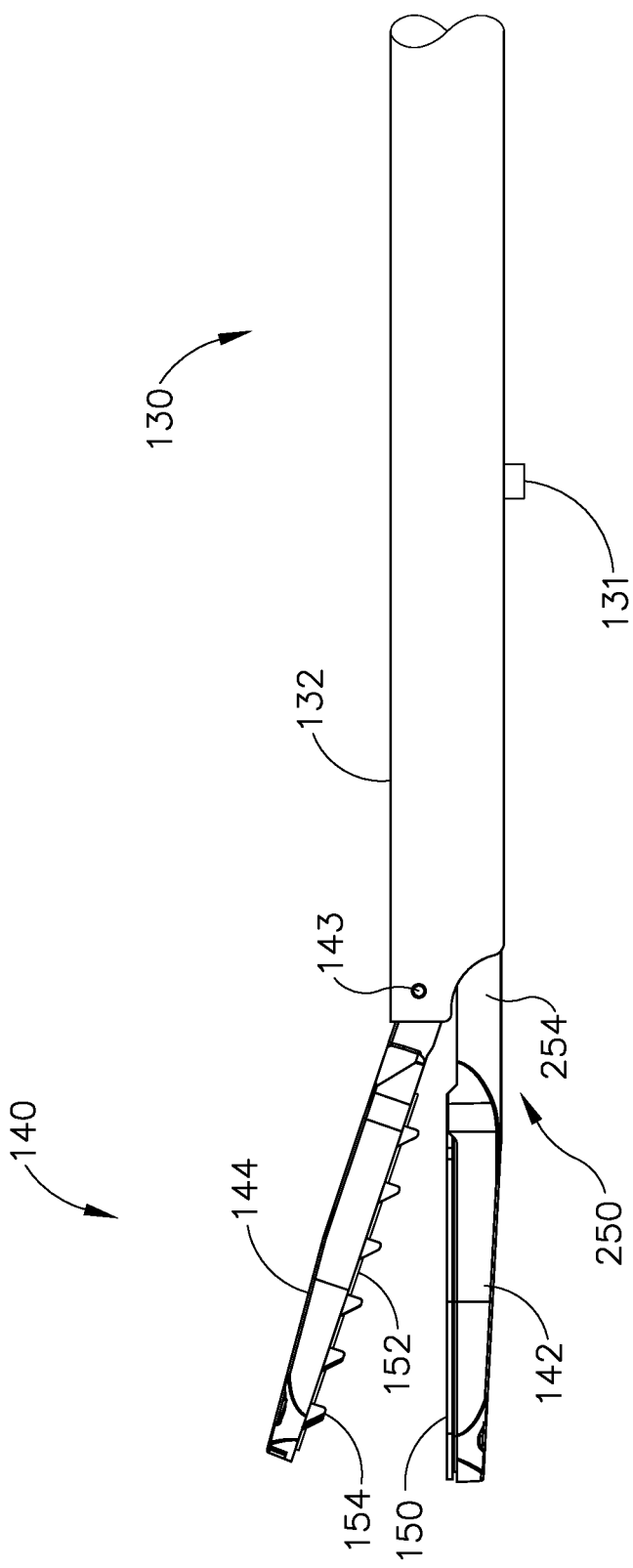
FIG. 12 depicts a side elevational view of a shaft assembly and end effector of the instrument of FIG. 6.
Figure 14:
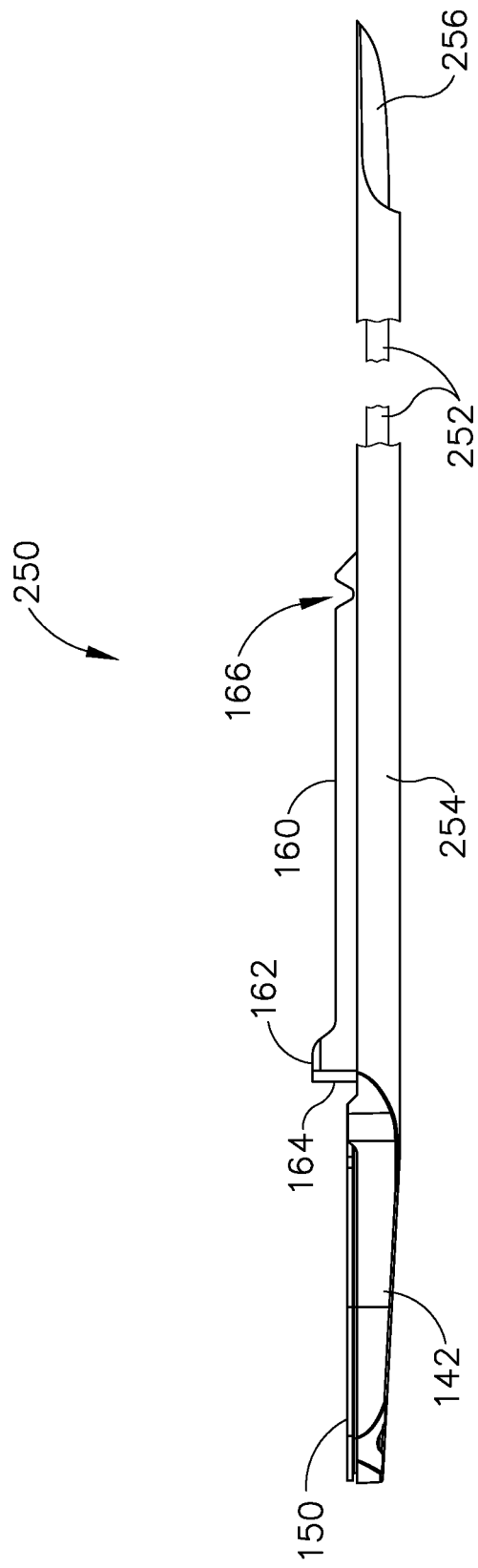
FIG. 14 depicts a side elevational view of the lower jaw assembly of FIG. 13.

As best seen in FIG. 14, lower jaw assembly (250) comprises an elongate electrical conductor (252). Conductor (252) is substantially encompassed within an insulating material (254) such that only a proximal end and a distal end of conductor (252) are exposed. Insulating material (254) may be sized to create a slight interference fit between sheath (132) and lower jaw assembly (250) to thereby selectively secure lower jaw assembly (250) within sheath (132) of shaft assembly (130). Additionally, lower jaw assembly (250) and sheath (132) may be keyed to one another to thereby limit or prevent rotation of lower jaw assembly (250) within shaft assembly (130). The distal end of conductor (252) is exposed relative to insulating material (254) to provide an electrode surface (150). As best seen in FIG. 12, with lower jaw assembly (250) disposed within shaft assembly (130), the distal end of lower jaw assembly (250), including electrode surface (150), is exposed relative to a distal end of shaft assembly (130) so as to provide a first jaw (142) of end effector (140) as will be discussed in more detail below. The proximal end of conductor (252) is exposed relative to insulating material (254) to provide an electrical contact (256). As best seen in FIGS. 10 and 11, with lower jaw assembly (250) disposed within shaft assembly (130), the proximal end of lower jaw assembly (250), including electrical contact (256), is exposed relative to the proximal end of sheath (132). As will be discussed in more detail below, electrical contact (256) of conductor (252) is operable to couple with an electrical source (180) via a cable (184), which is selectively coupleable to the proximal end of shaft assembly (130). Electrical source (180) is operable to deliver RF energy to electrode surface (150) via conductor (252) so as to coagulate or seal tissue in contact with electrode surface (150), as will be discussed in more detail below.

Figure 15:
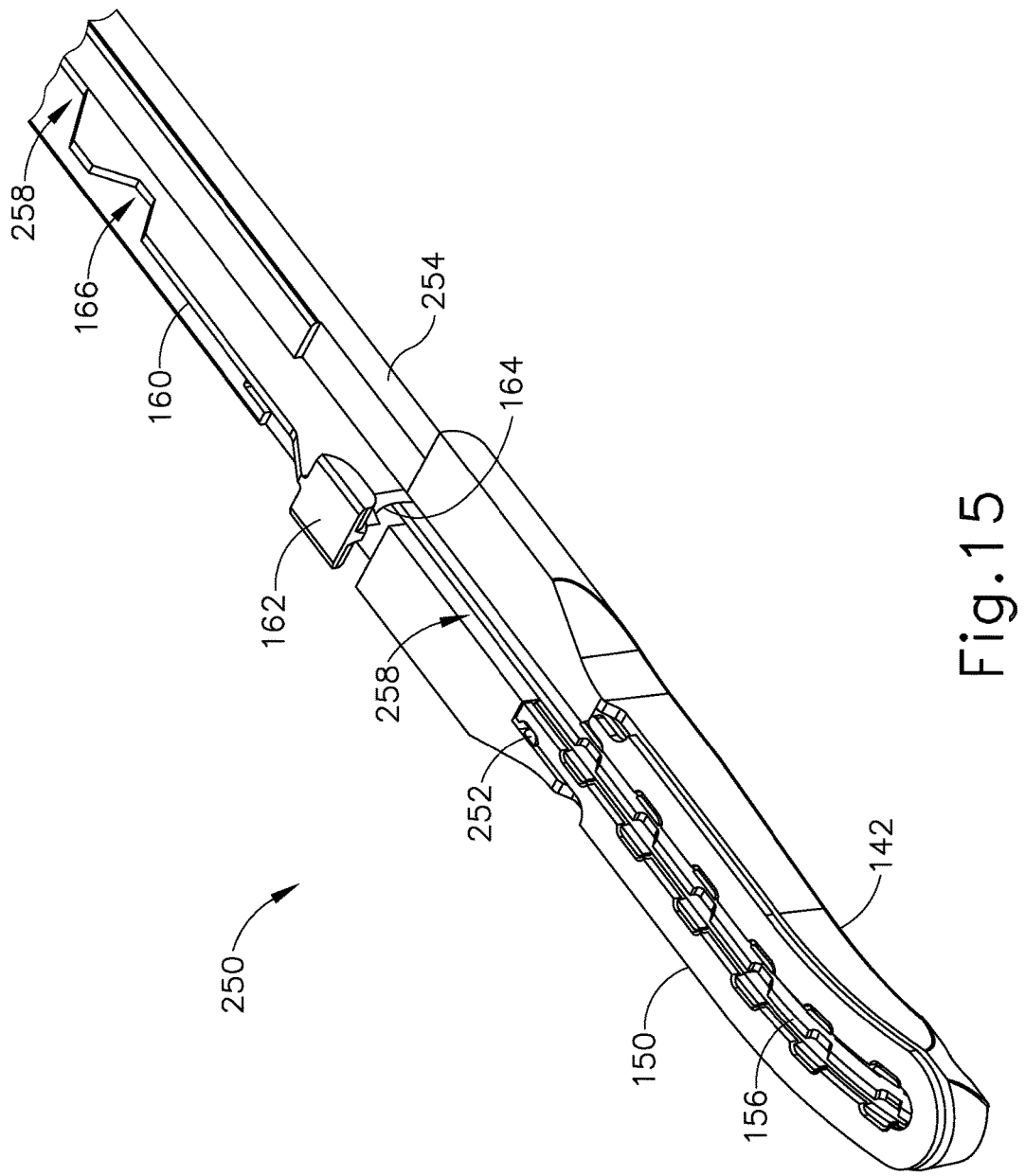
FIG. 15 depicts a perspective view of a distal portion of the lower jaw assembly of FIG. 13.

Lower jaw assembly (250) further comprises a firing beam (160) that is longitudinally movable along part of the length of lower jaw assembly (250). In particular, as best seen in FIG. 15, a top surface of lower jaw assembly (250) comprises an elongate slot (258) formed therein. Firing beam (160) is slidably disposed within slot (258) such that firing beam (160) is longitudinally translatable within slot (258). A distal end of firing beam (160) includes a sharp distal blade (164). Distal blade (164) is substantially sharp, such that distal blade (164) will readily sever tissue that is captured within end effector (140) between jaws (142, 144). In some versions of instrument (100), distal blade (164) may be electrically grounded to provide a return path for RF energy via contact with inner tube (136) as will be discussed in more detail below. Inner tube (136) may be grounded via contact with a ground wire within cable (184). In some other versions, distal blade (164) serves as an active electrode.

Figure 16A:
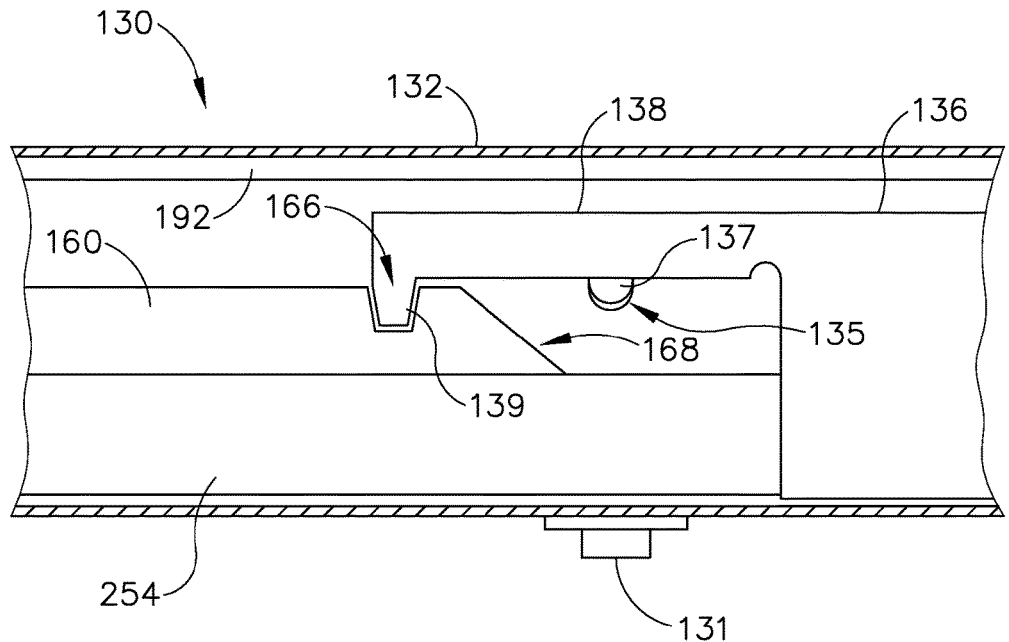
FIG. 16A depicts a cross-sectional side view of the shaft assembly of FIG. 12 with a firing beam of the lower jaw assembly of FIG. 13 engaged with an inner tube of the shaft assembly.
Figure 16B:
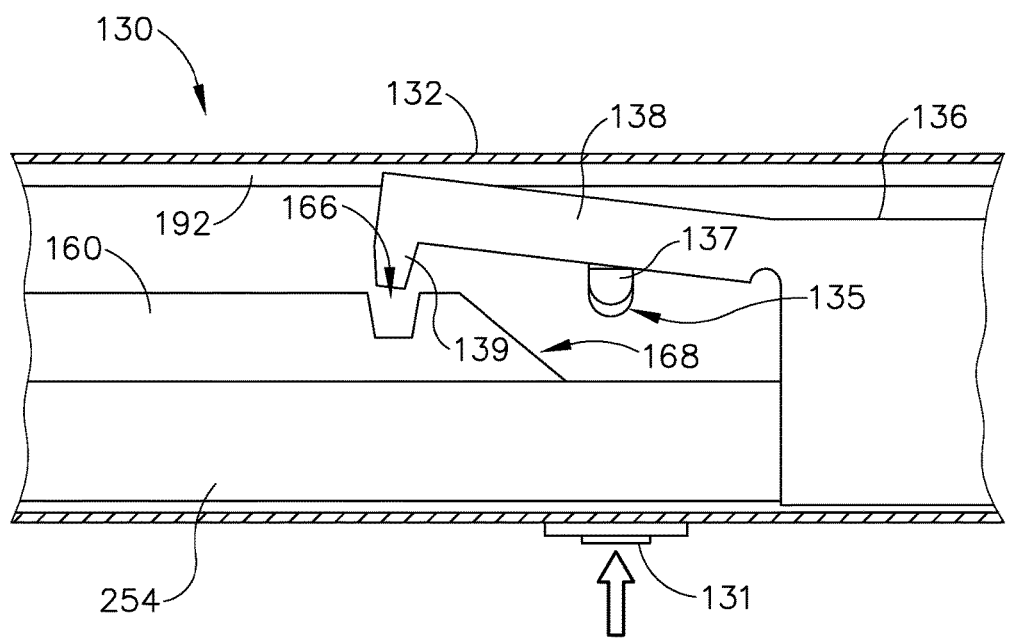
FIG. 16B depicts a cross-sectional side view of the shaft assembly of FIG. 12 with the firing beam of FIG. 16A disengaged from the inner tube of FIG. 16A.
Figure 17A:
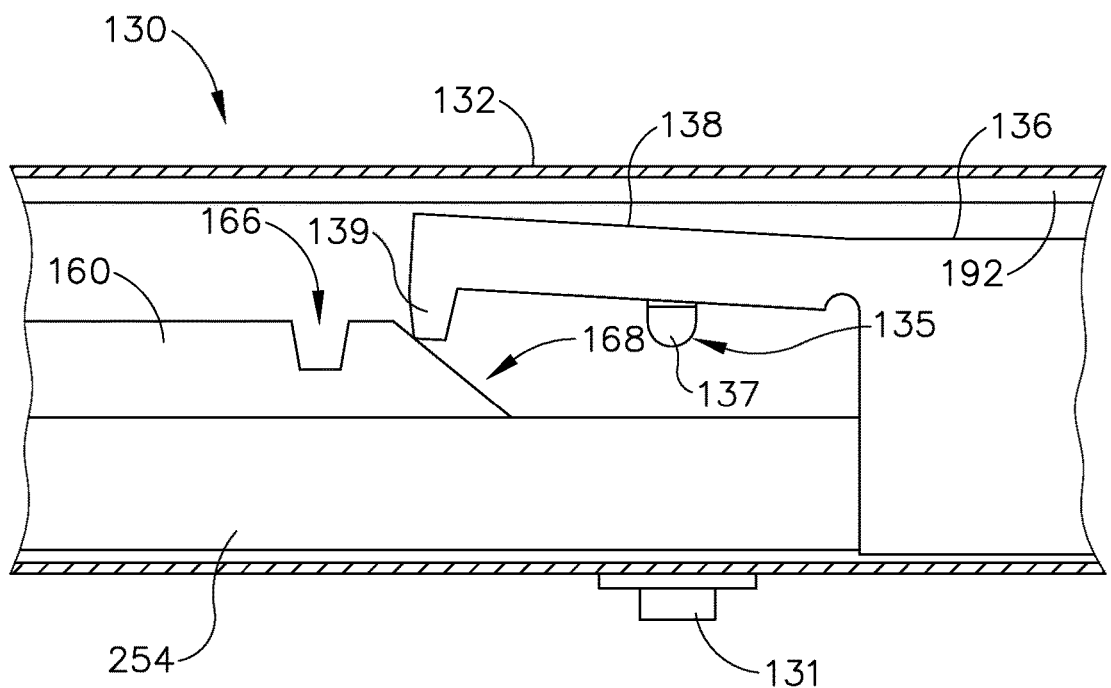
FIG. 17A depicts a cross-sectional side view of the shaft assembly of FIG. 12 with the firing beam of FIG. 16A at an initial stage of engagement with the inner tube of FIG. 16A.
Figure 17B:
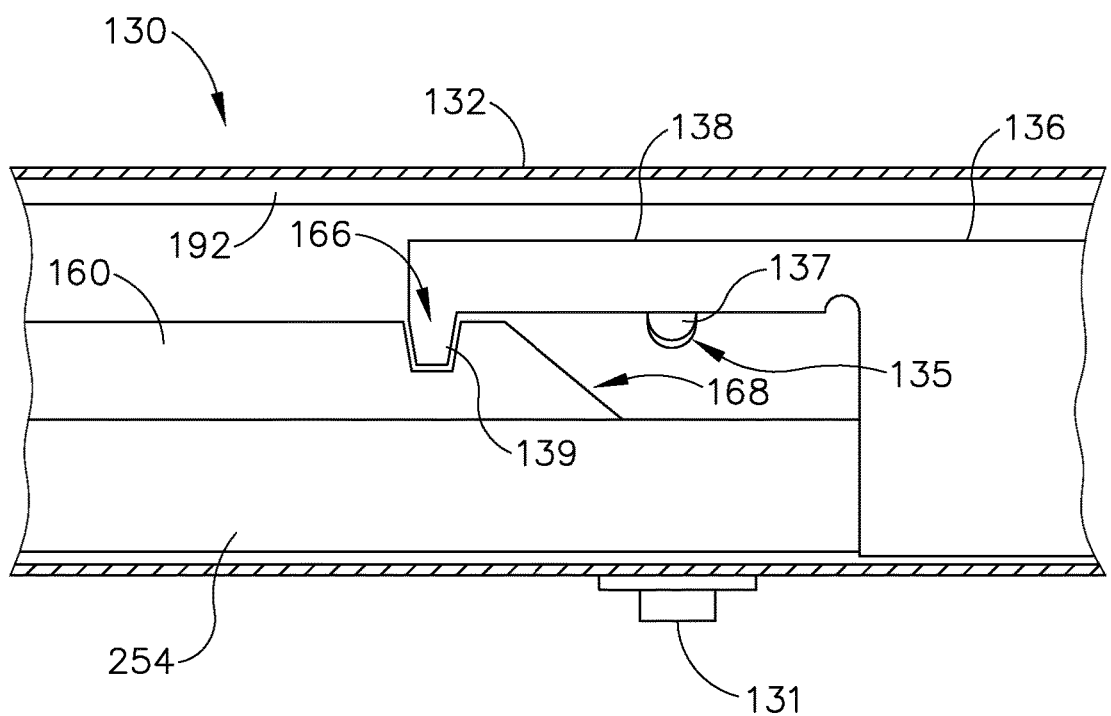
FIG. 17B depicts a cross-sectional side view of the shaft assembly of FIG. 12 with the firing beam of FIG. 16A driven proximally so as to fully engage the inner tube of FIG. 16A.

As mentioned above, inner tube (136) is slidably disposed within sheath (132). Inner tube (136) is coupled with trigger (124) such that inner tube (136) is longitudinally translatable relative to sheath (132) in response to pivoting of trigger (124) toward and away from pistol grip (122). In particular, inner tube (136) will translate longitudinally distally relative to sheath (132) in response to pivoting of trigger (124) toward pistol grip (124); and inner tube (136) will translate longitudinally proximally relative to sheath (132) in response to pivoting of trigger (124) away from pistol grip (122). As shown in FIGS. 16A-17B, a distal end of inner tube (136) comprises a resilient cantilevered arm (138). Cantilevered arm (138) is biased toward a substantially horizontal position as shown in FIGS. 16A and 17B. Cantilevered arm (138) comprises a tab (139) extending downwardly from a distal end of cantilevered arm (138). As best seen in FIGS. 14 and 15, a proximal end of firing beam (160) includes a notch (166). Tab (139) of cantilevered arm (138) is configured to be received within notch (166) to thereby couple firing beam (160) with inner tube (136) such that longitudinal translation of inner tube (136) causes concurrent longitudinal translation of firing beam (160). It should therefore be understood that with firing beam (160) coupled with inner tube (136), pivoting of trigger (124) toward pistol grip (124) causes distal longitudinal translation of firing beam (160) relative to sheath (132); and pivoting of trigger (124) away from pistol grip (124) causes proximal longitudinal translation of firing beam (160) relative to sheath (132). As will be discussed in greater detail below, shaft assembly (130) comprises a slidable button (131) that is operable to drive cantilevered arm (138) out of engagement with firing beam (160) to thereby decouple firing beam (160) from inner tube (136).

C. Exemplary End Effector

As discussed above, with lower jaw assembly (250) disposed within shaft assembly (130), the distal end of lower jaw assembly (250), including electrode surface (150), is exposed relative to a distal end of shaft assembly (130) so as to provide first jaw (142). End effector (140) of the present example comprises first jaw (142) and a second jaw (144) that are configured to operate substantially similar to first jaw (142) and second jaw (142) of end effector (40) discussed above except for the differences discussed below. In the present example, first jaw (142) is substantially fixed relative to shaft assembly (130) when tab (139) of cantilevered arm (138) is positioned within notch (166) of firing beam (160); while second jaw (144) pivots relative to shaft assembly (130), toward and away from first jaw (142). Use of the term "pivot" should not be read as necessarily requiring pivotal movement about a fixed axis. In some versions, second jaw (144) pivots about an axis that is defined by a pin (or similar feature) that slides along an elongate slot or channel as second jaw (144) moves toward first jaw (142). In such versions, the pivot axis translates along the path defined by the slot or channel while second jaw (144) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (144) about an axis that remains fixed and does not translate within a slot or channel, etc.

Figure 13:
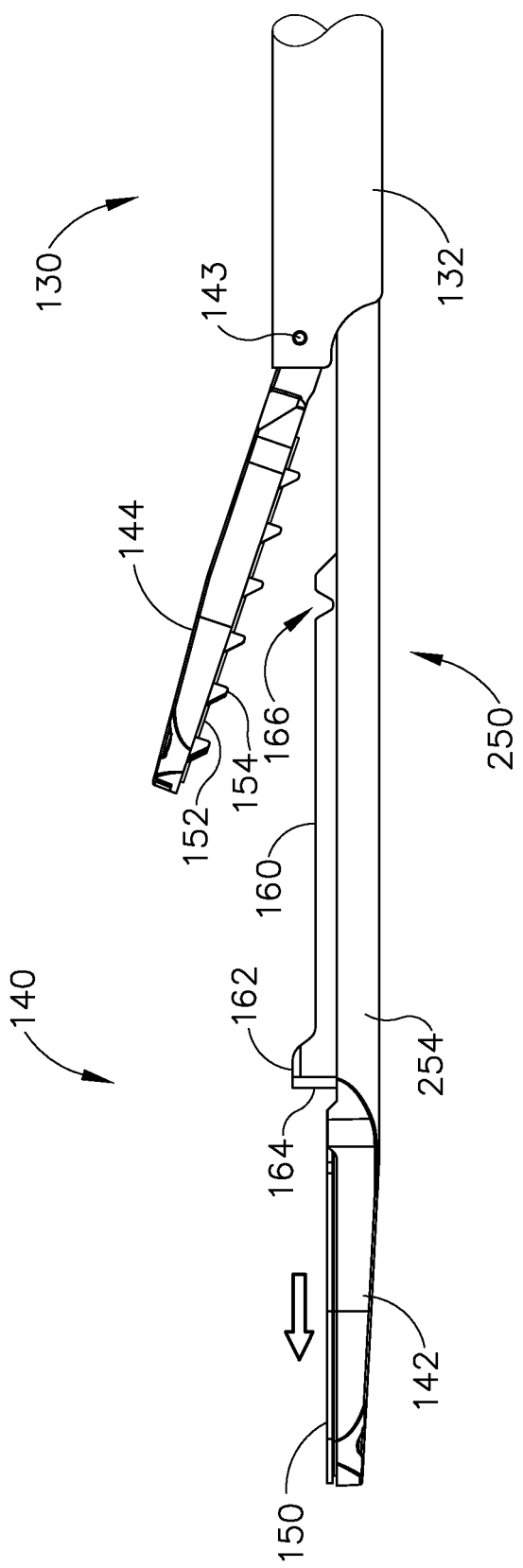
FIG. 13 depicts a side elevational view of the shaft assembly and end effector of FIG. 12 with a lower jaw assembly partially removed from the shaft assembly.

As best seen in FIG. 12, second jaw (144) is pivotably coupled with a distal end of sheath (132) via a pin (143). Second jaw (144) is coupled with trigger (124) such that second jaw (144) is pivotable toward and away from first jaw (142) in response to pivoting of trigger (124) toward and away from pistol grip (122). In particular, second jaw (144) is pivotable toward first jaw (142) in response to pivoting of trigger (124) toward pistol grip (124); and such that second jaw (144) is pivotable away from first jaw (142) in response to pivoting of trigger (124) away from pistol grip (122). In some versions, actuators such as rods or cables, etc., may extend through sheath (132) and be joined with second jaw (144), such that longitudinal movement of the actuator rods/cables/etc. through shaft assembly (130) provides pivoting of second jaw (144) about pin (143) relative to shaft assembly (130) and relative to first jaw (142). Of course, jaws (142, 144) may instead have any other suitable kind of movement and may be actuated in any other suitable fashion. For instance, as shown in FIGS. 13-15, firing beam (160) of the present example comprises an upper flange (162) that is configured to operate substantially similar to upper flange (62) of firing beam (60) discussed above. Firing beam (160) further comprises a lower flange (not shown) slidably disposed within lower jaw assembly (250) below slot (258) and configured to operate substantially similar to lower flange (66) of firing beam (60) discussed above. As with firing beam (60) discussed above, upper flange (162) and the lower flange provide firing beam (160) with an "I-beam" type of configuration. The "I-beam" type of configuration of firing beam (160) provides closure of jaws (142, 144) as firing beam (160) is advanced distally. In particular, with lower jaw assembly (250) disposed within shaft assembly (130), upper flange (162) is operable to engage second jaw (144) as firing beam (160) is advanced distally such that flange (162) urges second jaw (144) pivotally toward first jaw (142) as firing beam (160) is advanced distally by bearing against second jaw (144).

As discussed above, the distal end of conductor (252) is exposed relative to insulating material (254) to provide electrode surface (150). Furthermore, the proximal end of conductor (252) is exposed relative to insulating material (254) to provide electrical contact (256). With lower jaw assembly (250) disposed within shaft assembly (130), the proximal end of lower jaw assembly (250), including electrical contact (256), is exposed relative to a proximal end of sheath (132). Electrode surface (150) is in communication with an electrical source (180) via electrical contact (256). An underside of second jaw (144) presents another electrode surface (152). Electrode surface (152) is in communication with electrical source (180) via an electrical conductor (192) that extends along the length of shaft assembly (130) and provides an electrical contact (257) that is exposed relative to the proximal end of sheath (132) adjacent electrical contact (256).

Electrical contacts (256, 257) are coupled with electrical source (180) via cable (184), which couples with the proximal end of sheath (132). In particular, as best seen in FIG. 7, a distal end of cable (184) comprises an integral plug (185), which is operable to selectively couple with or about threads (133) of sheath (132). For instance, an interior of plug (185) may comprise threading (not shown) operable to threadably couple with threading (133) of sheath (132). Alternatively, plug (185) may couple about threads (133) of sheath (132) in a snap-fit or friction-fit manner, or any other appropriate manner as would be apparent to one of ordinary skill in the art in view of the teachings herein. An interior of plug (185) comprises a plurality of electrical contacts (not shown) operable to provide electrical continuity between electrical contacts (256, 257) and electrical conduits of cable (184). Thus, it should be appreciated that plug (185) is operable to provide electrical continuity between electrode surfaces (150, 152) and electrical source (180) when coupled with sheath (132). Electrical source (180) is operable to deliver RF energy to electrode surface (150) at an active polarity while electrode surface (152) serves as a reference/return passive electrode, such that RF current flows between electrode surfaces (150, 152) and thereby through tissue captured between jaws (142, 144). There are instances where the active signal crosses zero potential that the reference is at the same potential so there is no current flow. Electrical source (180) may be external to electrosurgical instrument (100) or may be integral with electrosurgical instrument (100) (e.g., activation assembly (200), etc.), as described in one or more references cited herein or otherwise.

Activation assembly (200) comprises a cable (212) that is operable to couple activation assembly (200) with cable (184) which in turn couples activation assembly (200) with electrical source (180). In particular, a proximal end of cable (212) comprises an integral plug (214). Plug (185) of cable (184) comprises a socket (187) that is operable to selectively receive an electrical contact (216) of plug (214) so as to provide electrical continuity between activation assembly (200) and electrical conduits of cable (184), which in turn provides electrical continuity between electrical source (180) and electrode surfaces (150, 152). Thus, it should be appreciated that cable (212) is operable to provide electrical continuity between activation assembly (200) and electrical source (180); and is thereby operable to selectively activate electrode surfaces (150, 152). Activation assembly (200) further comprises a plurality of buttons (210) that are oriented along, and exposed relative to, an exterior surface of each flange (204). Buttons (210) of activation assembly (200) are operable to regulate delivery of power from electrical source (180) to electrode surfaces (150, 152). For instance, buttons (210) may be activated to deliver RF energy to electrode surfaces (150, 152), to change the frequency of RF energy delivered to electrode surfaces (150, 152), or to perform/control any other function as would be apparent to one of ordinary skill in the art in view of the teachings herein. In some versions, one button (210) may provide RF energy at a first frequency and/or amplitude while another button (210) provides RF energy at a second frequency and/or amplitude. Other suitable operability that may be provided through buttons (210) will be apparent to those of ordinary skill in the art in view of the teachings herein. It should also be understood that electrode surfaces (150, 152) may be provided in a variety of alternative locations, configurations, and relationships. In some versions, activation assembly (200) also serves as an electrical lockout against trigger (124), such that trigger (124) cannot be fully actuated unless one or more buttons (210) are being pressed simultaneously. Examples of how such a lockout may be provided are disclosed in one or more of the references cited herein. In addition or in the alternative, trigger (124) may serve as an electrical lockout against one or more buttons (210), such that buttons (210) cannot be effectively activated unless trigger (124) is being squeezed simultaneously.

By way of example only, power source (180) and/or activation assembly (200) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued the May 26, 2015, disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (180) and activation assembly (200) will be apparent to those of ordinary skill in the art in view of the teachings herein.

As best seen in FIGS. 12 and 13, the lower side of second jaw (144) includes a plurality of teeth serrations (154). It should be understood that the upper side of first jaw (142) may include complementary serrations (156) within which serrations (154) may nest, to enhance gripping of tissue captured between jaws (142, 144) without necessarily tearing the tissue. In other words, it should be understood that serrations (154, 156) may be generally blunt or otherwise atraumatic. In the present example, serrations (156) of first jaw (142) are mainly recesses; while serrations (154) of second jaw (144) are mainly protrusions. Of course, serrations (154, 156) may take any other suitable form or may be simply omitted altogether. It should also be understood that serrations (154, 156) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (142, 144). In some versions, serrations (154, 156) are electrically conductive.

With jaws (142, 144) in a closed position, shaft assembly (130) and end effector (140) are sized and configured to fit through trocars having various inner diameters, such that electrosurgical instrument (100) is usable in minimally invasive surgery, though of course electrosurgical instrument (100) could also be used in open procedures if desired. By way of example only, with jaws (142, 144) in a closed position, shaft assembly (130) and end effector (140) may present an outer diameter of approximately 5 mm. Alternatively, shaft assembly (130) and end effector (140) may present any other suitable outer diameter (e.g., between approximately 2 mm and approximately 20 mm, etc.).

As another merely illustrative variation, either jaw (142, 144) or both of jaws (142, 144) may include at least one port, passageway, conduit, and/or other feature that is operable to draw steam, smoke, and/or other gases/vapors/etc. from the surgical site. Such a feature may be in communication with a source of suction, such as an external source or a source within handpiece (120), etc. In addition, end effector (140) may include one or more tissue cooling features (not shown) that reduce the degree or extent of thermal spread caused by end effector (140) on adjacent tissue when electrode surfaces (150, 152) are activated. By way of example only, electrosurgical instrument (100) may be constructed and operable to provide liquid coolant to end effector (140) in accordance with at least some of the teachings of U.S. patent application Ser. No. 14/553,329, entitled "Features to Drive Fluid Toward an Ultrasonic Blade of a Surgical Instrument," filed Nov. 25, 2014, now U.S. Pat. No. 10,004,529, issued Jun. 26, 2018, the disclosure of which is incorporated by reference herein. Various other suitable forms that such cooling features may take will be apparent to those of ordinary skill in the art in view of the teachings herein.

In some versions, end effector (140) includes one or more sensors (not shown) that are configured to sense a variety of parameters at end effector (140), including but not limited to temperature of adjacent tissue, electrical resistance or impedance of adjacent tissue, voltage across adjacent tissue, forces exerted on jaws (142, 144) by adjacent tissue, etc. By way of example only, end effector (140) may include one or more PTC thermistor bodies (not shown) (e.g., PTC polymer, etc.), located adjacent to electrodes (150, 52) and/or elsewhere. Data from sensors may be communicated to activation assembly (200). Activation assembly (200) may process such data in a variety of ways. By way of example only, activation assembly (200) may modulate or otherwise change the RF energy being delivered to electrode surfaces (150, 152), based at least in part on data acquired from one or more sensors at end effector (140). In addition or in the alternative, activation assembly (200) may alert the user to one or more conditions via an audio and/or visual feedback device (e.g., speaker, lights, display screen, etc.), based at least in part on data acquired from one or more sensors at end effector (140). It should also be understood that some kinds of sensors need not necessarily be in communication with activation assembly (200), and may simply provide a purely localized effect at end effector (140). For instance, the PTC thermistor bodies at end effector (140) may automatically reduce the energy delivery at electrode surfaces (150, 152) as the temperature of the tissue and/or end effector (140) increases, thereby reducing the likelihood of overheating. In some such versions, a PTC thermistor element is in series with power source (180) and electrode surface (150, 152); and the PTC thermistor provides an increased impedance (reducing flow of current) in response to temperatures exceeding a threshold. Furthermore, it should be understood that electrode surfaces (150, 152) may be used as sensors (e.g., to sense tissue impedance, etc.). Various kinds of sensors that may be incorporated into electrosurgical instrument (100) will be apparent to those of ordinary skill in the art in view of the teachings herein. Similarly various things that can be done with data from sensors, by activation assembly (200) or otherwise, will be apparent to those of ordinary skill in the art in view of the teachings herein. Other suitable variations for end effector (140) will also be apparent to those of ordinary skill in the art in view of the teachings herein.

D. Sterilization

After use of instrument (100), it may be desirable to sterilize handpiece (120), shaft assembly (130) (including lower jaw assembly (250)), and/or end effector (140). To sterilize instrument (100) after use, activation assembly (200) is disconnected from cable (184) and decoupled from handpiece (120). Because the electrical components of instrument (100) are housed within activation assembly (200), with activation assembly decoupled from handpiece (120), handpiece (120) is void of any electrical components that may be damaged during sterilization. At this point, cover (128) of handpiece (120) is removed to expose the interior of handpiece (120) and any components of instrument (100) disposed therein. As shown in FIG. 10, cover (128) may be coupled with handpiece (120) in a manner (e.g., a snap-fit manner) such that cover (128) may be completely removed from handpiece. Alternatively, cover (128) may be hingedly coupled with handpiece (120) as shown in FIG. 11, or in any other appropriate manner as would be apparent to those of ordinary skill in the art in view of the teachings herein. With cover (128) removed from handpiece (120), the interior of handpiece (120) and any components of instrument (100) disposed therein may be sterilized via opening (129) of handpiece (120). In addition, an exterior of handpiece (120) or another other region of handpiece (120) may be sterilized at this point.

Lower jaw assembly (250) of shaft assembly (130) is removed before the interior of handpiece (120) is sterilized. As best seen in FIGS. 16A-17B, shaft assembly (130) comprises a slidable button (131) projecting from an exterior surface of sheath (132). A transverse arm (137) of button (131) is slidably disposed within a slot (135) of sheath (132). Transverse arm (137) is operable to translate within slot (135) so as to engage an underside of cantilevered arm (138) to thereby drive cantilevered arm (138) out of engagement with firing beam (160) such that firing beam (160) is decoupled from inner tube (136) and such that lower jaw assembly (250) may be slidably removed from shaft assembly (130). FIG. 16A shows lower jaw assembly (250) disposed within shaft assembly (130). In this position, firing beam (160) is coupled with inner tube (136) via tab (139) of cantilevered arm (138) and notch (166) as discussed above. To remove lower jaw assembly (250), firing beam (160) must be decoupled from inner tube (136). In order to decouple firing beam (160) from inner tube (136), slidable button (131) is depressed so as to cause a translation of transverse arm (137) within slot (135) to thereby drive cantilevered arm (138) out of engagement with firing beam (160) as shown in FIG. 16B. At this point, lower jaw assembly (250) may be removed from shaft assembly (130) for sterilization or replacement.

While slidable button (131) of the present example is shown as projecting outwardly from sheath (132) when slidable button (131) is not actuated in the present example, in some other versions of instrument (100), slidable button (131) may be flush with sheath (132) when slidable button (131) is not actuated. In some such versions, button (131) may be recessed relative to sheath (132) when slidable button (131) is actuated. In some other variations, button (131) moves longitudinally along a path that is parallel to the longitudinal axis of shaft assembly (130) in order to decouple firing beam (160) from inner tube (136). As yet another merely illustrative example, a variation of button (131) may be provided at handpiece (120) instead of being positioned on shaft assembly (130). Various suitable components may be used to link such a user input feature at handpiece (120) with a feature that drives cantilevered arm (138) out of engagement with firing beam (160).

Figure 18:
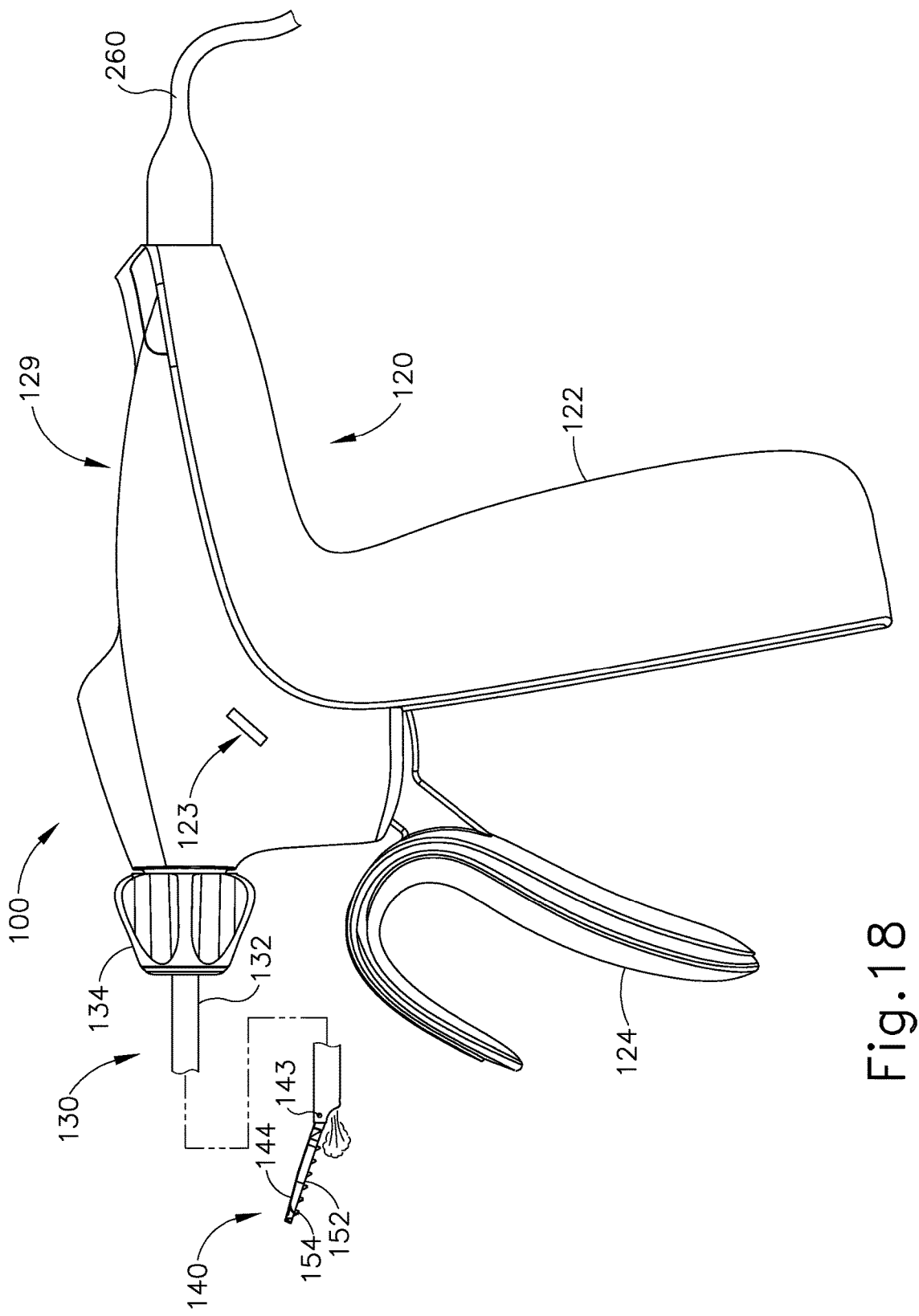
FIG. 18 depicts a side elevational view of the instrument of FIG. 6 with a flushing hose coupled with a proximal portion of the instrument while the lower jaw assembly of FIG. 13 is removed from the instrument.

With lower jaw assembly (250) removed from shaft assembly (130), the hollow interior of sheath (132) is substantially unobstructed. At this point, as shown in FIG. 18, a flushing hose (260) may be coupled with the proximal end of sheath (132) via threads (133). Flushing hose (260) may provide, among other things, high pressure steam to the hollow interior of sheath (132) to thereby sterilize the interior components of shaft assembly (130). In addition, an exterior of shaft assembly (130) or any other region of shaft assembly (130) may be sterilized. Furthermore, end effector (140) may be sterilized at this point. Furthermore, with lower jaw assembly (250) removed from shaft assembly (130), firing beam (160) may be removed from lower jaw assembly (250) for separate cleaning or for replacement. For instance, in some versions of lower jaw assembly (250), firing beam (160) may be slid proximally through slot (258) so as to remove firing beam (160) from lower jaw assembly (250)

After shaft assembly (130) and lower jaw assembly (250) have been sterilized, lower jaw assembly (250) may be reinserted into shaft assembly (130) for use in subsequent surgical procedures. Alternatively, a new lower jaw assembly (250) may be inserted into shaft assembly (130). In either case, a proximal end of firing beam (160) comprises an angled surface (i.e., a ramp) (168). As shown in FIG. 17A, as lower jaw assembly (250) is slid into shaft assembly (130), contact between tab (139) of cantilevered arm (138) and angled surface (168) of firing beam (160) drives cantilevered arm (138) upwardly until tab (139) aligns with notch (166). At this point, tab (139) is received within notch (166) as cantilevered arm (138) returns toward the position shown in FIGS. 16A and 17B, thereby once again coupling firing beam (160) with inner tube (136). At this point, cover (128) may be coupled with handpiece (120) once again to thereby cover opening (129) and effectively close handpiece (120). Activation assembly (200) may then be recoupled with handpiece (120) and reconnected to cable (184) via cable (212). At this point, instrument (100) is sterilized and ready for use.

In some instances, a user may wish to refrain from coupling actuation assembly (200) within handpiece (120). In such instances, the user may wish to provide selective activation of instrument (100) via a footswitch assembly, an external controller, or some other input device that is configured to operate substantially similar to activation assembly (200).

It should be understood that, although instrument (100) is primarily discussed above as being sterilized using high pressure steam, any other method or manner of sterilizing instrument (100) may be used as would be apparent to those of ordinary skill in the art in view of the teachings herein.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus for operating on tissue, wherein the apparatus comprises:
   (a) a body,
   (b) a shaft assembly extending distally from the body, wherein the shaft assembly defines a longitudinal axis, wherein the shaft assembly comprises:
      (i) an outer sheath, and
      (ii) a lower jaw assembly, wherein the lower jaw assembly is slidably disposed within the outer sheath such that the lower jaw assembly is selectively removable from the outer sheath along a path that is parallel to the longitudinal axis, wherein the lower jaw assembly comprises an electrical conductor assembly having a proximal end and a distal end, wherein the distal end of the conductor provides a first electrode surface; and
   (c) an end effector, wherein the end effector comprises an upper jaw pivotably coupled with the shaft assembly, wherein the upper jaw comprises a second electrode surface, wherein the upper jaw is operable to pivot toward and away from the lower jaw to thereby capture tissue between the upper jaw and the distal end of the conductor;
   wherein the first and second electrode surfaces are operable to deliver RF energy to tissue captured between the upper jaw and the lower jaw;
   wherein the lower jaw assembly further comprises a firing beam, wherein the firing beam is operable to translate longitudinally within the lower jaw assembly; and
   wherein the lower jaw assembly and at least a portion of the firing beam are selectively removable from the shaft assembly along a distal direction extending opposite the shaft assembly while the upper jaw remains coupled with the shaft assembly.

2. The apparatus of claim 1, wherein the body further comprises an activation assembly having at least one user input feature, wherein the at least one user input feature is operable to selectively provide delivery of RF energy to tissue captured between the upper jaw and the lower jaw via the first and second electrode surfaces.

3. The apparatus of claim 2, wherein the body further comprises a handpiece housing, wherein the activation assembly is removably coupled with the handpiece housing.

4. The apparatus of claim 3, wherein the activation assembly comprises a base and a pair of resilient flanges.

5. The apparatus of claim 2, further comprising a primary cable assembly removably coupled with the body, wherein the primary cable assembly is operable to provide electrical power to the first and second electrode surfaces.

6. The apparatus of claim 5, wherein the activation assembly further comprises a secondary cable assembly in communication with the at least one user input feature, wherein the secondary cable assembly is removably coupled with the primary cable assembly.

7. The apparatus of claim 1, wherein the electrical conductor of the lower jaw assembly is substantially encompassed within an insulating material.

8. The apparatus of claim 1, wherein the shaft assembly further comprises a translatable actuation member, wherein the translatable actuation member is slidably disposed within the outer sheath, wherein the translatable actuation member is configured to selectively couple with the firing beam such that longitudinal translation of the translatable actuation member causes concurrent longitudinal translation of the firing beam.

9. The apparatus of claim 8, wherein the translatable actuation member is selectively coupleable with the firing beam in a snap-fit manner.

10. The apparatus of claim 8, wherein the shaft assembly comprises a button operable to decouple the translatable actuation member from the firing beam.

11. The apparatus of claim 1, wherein the body comprises a cover operable to selectively expose an interior of the body.

12. The apparatus of claim 11, wherein the cover is hingedly coupled with the body.

13. The apparatus of claim 1, wherein the body further comprises a coupling feature, the apparatus further comprising a cable assembly removably coupled with the coupling feature, wherein the cable assembly is operable to provide electrical power to the first and second electrode surfaces.

14. The apparatus of claim 13, wherein the coupling feature further comprises a fluid port, wherein the fluid port is configured to receive fluid to thereby flush at least a portion of the shaft assembly after removal of the cable assembly from the coupling feature.

15. The apparatus of claim 1, wherein the shaft assembly further comprises a button, wherein a transverse arm of the button is slidably disposed within a slot of the outer sheath, wherein the transverse arm is operable to translate within the slot so as to engage an underside of a cantilevered arm to thereby drive the cantilevered arm out of engagement with the firing beam such that the firing beam is decoupled from an inner tube of the shaft assembly and such that the lower jaw assembly is capable of being slidably removed from the shaft assembly along the distal direction.

16. An apparatus for operating on tissue, wherein the apparatus comprises:
(a) a body including an interior cavity and an exterior surface;
(b) an activation assembly including an interior cavity and an exterior surface, wherein the electrial components of the apparatus are housed within the interior cavity of the activation assembly;
(c) an end effector, wherein the end effector comprises at least one electrode surface, wherein the at least one electrode surface is operable to apply RF energy to tissue, wherein the activation assembly is operable to regulate the delivery of power to the electrode surfaces; and
(d) a shaft assembly, wherein the shaft assembly extends distally from the body, wherein the end effector is located at a distal end of the shaft assembly,
wherein the exterior surface of the activation assembly includes a plurality of coupling features that are configured to couple with a corresponding plurality of coupling features of the exterior surface of the body to selectively couple the activation assembly with the body.

17. The apparatus of claim 16, wherein the exterior surface of the activation assembly comprises a plurality of tabs operable to couple the activation assembly with the body and to limit movement of the activation assembly.

18. The apparatus of claim 16, further comprising:
a shaft assembly extending distally from the body, wherein the shaft assembly comprises:
(i) an outer sheath; and
(ii) a lower jaw assembly, wherein the lower jaw assembly is slidably disposed within the outer sheath such that the lower jaw assembly is selectively removable from the outer sheath;
wherein the end effector comprises an upper jaw pivotably coupled with the shaft assembly; and
wherein the lower jaw assembly is selectively removable from the shaft assembly along a distal direction extending opposite the shaft assembly while the upper jaw remains coupled with the shaft assembly.

19. A method of sterilizing an electrosurgical instrument, wherein the instrument comprises a body, a removable activation assembly, and an end effector, wherein the activation assembly is operable to regulate the delivery of power to the end effector, the method comprising the steps of:
(a) removing a cover of the body, wherein the step of removing a cover of the body exposes an interior of the body;
(b) decoupling the activation assembly from the body and removing the activation assembly from the body to thereby make the instrument void of electrical components that are damageable during sterilization; and
(c) sterilizing the instrument after removing the activation assembly as the instrument is now void of electrical components damageable during the sterilization.

20. The method of claim 18, wherein the instrument further comprises a shaft assembly, wherein the method further comprises:
(a) removing a lower jaw assembly from the shaft assembly; and
(b) sterilizing a hollow interior of the shaft assembly.

* * * * *